(12) United States Patent
Reichman et al.

(10) Patent No.: US 6,310,113 B1
(45) Date of Patent: Oct. 30, 2001

(54) APPARATUS AND METHODS FOR PRODUCING SUPERABSORBENT FOAMS

(75) Inventors: Eliezer Reichman; Arkday Skibinsky, both of Rehovot; Diana Kumin, Rishon Leziion, all of (IL)

(73) Assignee: Nova-Sorb Ltd., Holon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/101,315

(22) PCT Filed: Dec. 18, 1996

(86) PCT No.: PCT/IL96/00183

§ 371 Date: Sep. 14, 1998

§ 102(e) Date: Sep. 14, 1998

(87) PCT Pub. No.: WO97/24090

PCT Pub. Date: Jul. 10, 1997

Related U.S. Application Data

(63) Continuation-in-part of application No. 08/574,964, filed on Dec. 19, 1995, now Pat. No. 5,859,077.

(51) Int. Cl.⁷ .................................................. A61F 13/15
(52) U.S. Cl. .................... 521/149; 264/45.1; 366/243; 366/244; 366/276; 366/279; 366/341; 366/342; 521/50; 521/50.5; 521/84.1; 521/149; 604/358; 604/369; 604/370; 604/372

(58) Field of Search ............................ 264/45.1; 366/243, 366/244, 276, 279, 341, 342; 521/84.1, 149, 50, 50.5; 604/358, 369, 370, 372

(56) References Cited

U.S. PATENT DOCUMENTS

| 3,980,280 | 9/1976 | Benson . |
| 5,328,935 | 7/1994 | Van Phan et al. . |
| 5,334,621 | 8/1994 | Beshouri . |
| 5,338,766 | 8/1994 | Phan et al. . |
| 5,372,766 | 12/1994 | Roe . |

FOREIGN PATENT DOCUMENTS

| 0295438 A | 12/1988 | (EP) . |
| 60221441 a | 11/1985 | (JP) . |
| WO/95/05204 | 8/1994 | (WO) . |

OTHER PUBLICATIONS

Riccardo Po, "Water –Absorbent Polymers : A Patent Survey", Journal of Macromolecular Science, Reviews Macromolecular Chemistry, 1994, C34(4), pp. 607–662.

Timothy J. Mason published by Ellis Hormond Ltd. "Practical Sonochemistry" sec. 4. 3 1991.

*Primary Examiner*—John M. Cooney, Jr.
(74) *Attorney, Agent, or Firm*—Eitan, Pearl, Latzer & Cohen-Zedek

(57) ABSTRACT

A method and apparatus for producing superabsorbent foam wherein the method includes forming a reaction mixture comprising a superabsorbent foam forming composition, stirring, and applying mechanical waves to form a superabsorbent foam.

33 Claims, 17 Drawing Sheets

APPARATUS AND METHODS FOR PRODUCING SUPERABSORBENT FOAMS

This Application is a 371 of PCT/IL96/00183 filed Dec. 18, 1996 and a continuation of Ser. No. 08/574,964 filed Dec. 19, 1995, U.S. Pat. No. 5,859,077

FIELD OF INVENTION

The present invention relates to apparatus and a method for forming porous superabsorbent materials generally and more particularly to apparatus and a method for producing superabsorbent foams.

BACKGROUND OF THE INVENTION

Superabsorbent polymeric materials capable of absorbing large quantities of liquids are known in the art and used in many applications, in particular in sick-care and hygienic products such as wound dressings, diapers, adult incontinence pads, feminine sanitary pads and the like. Prior art methods for producing superabsorbent materials capable of absorbing water are based on the use of highly hydrophilic polymers, such as polyacrylates, polyacrylamides, acrylates and their derivatives, grafted on starch or cellulose. Polymeric molecules are usually crosslinked and form a gel-like three-dimensional network. These methods are described in an article entitled Water-absorbent polymers: a patent survey, published in the Journal of Macromolecular Science, Reviews Macromolecular Chemistry, 1994, C34, 607–662.

The water absorbing capacity (WAC) of water-absorbing polymers can be substantially increased by forming pores (preferably open-cell pores) within the polymer matrix. Prior art methods of making porous polymer matrices are based on foaming the reaction mixture before or during the run of polymerization and/or crosslinking reactions using a blowing agent, such as gases or volatile liquids. A method of making superabsorbent polymer foam having improved absorptive properties is described, for example, in U.S. Pat. Nos. 5,328,935 and 5,338,766 to Vah Phan et at.

Other prior art approaches for forming porous absorbent materials include crosslinking of a multiplicity of precursor particles into an interparticle macroaggregate (U.S. Pat. No. 5,372,766 to Roe), freezing hydrophilic polymers solutions in the form of prenucleated ice sheets with subsequent freeze-drying (PCT publication No. WO 95/05204 to Schonfeldt et al), carrying out polymerization reactions in conditions of a specific type of high internal phase emulsion (U.S. Pat. No. 5,334,621 to Beshouri).

Prior art methods of preparing highly superabsorbent porous materials, also termed herein superabsorbent foams, having high WAC are deficient in some respects. For example, each of the prior art methods can be applied only to polymers of a definite chemical nature. Also, the possibility of fine controlling the parameters of the porous structure are limited, in particular on scaling up these methods for industrial applications.

SUMMARY OF THE INVENTION

A primary object of the present invention is to provide apparatus and a method for producing superabsorbent foams applicable to a variety of different polymers.

A further object of the present invention is to provide a superabsorbent foam made of any reaction mixture capable of forming a superabsorbent foam and having high absorption capabilities of fluids comprising of both low and high molecular weight components, such as urine and blood, respectively.

Another object of the present invention is to provide superabsorbent foams made from a wide range of synthetic and/or natural polymers, such as polyacrylates and collagen.

Yet another object of the present invention is to provide a method for forming superabsorbent foams which includes the application of physical forces to a precursor reaction mixture of the polymer foam.

A further object of the present invention is to provide apparatus for forming superabsorbent foams which includes a novel chemical reactor capable of producing the superabsorbent foams of the present invention on an industrial scale.

According to one aspect of the present invention, the suitable chemical reaction mixtures are exposed to steps of physical treatment in a reactor to produce a superabsorbent foam comprising a branched system of interconnecting pores which form a highly porous structure.

According to another aspect of the invention, the foam properties are controlled by applying mechanical waves of controllable frequency, amplitude and wave form. These waves may be periodic waves, such as sinusoidal waves having frequencies from hundreds of Hz to few dozens of KHz i.e., in the sound and near ultrasound range.

According to a further aspect of the present invention, mechanical waves application is used not only during foam formation and solidification but also at further stages of producing the porous superabsorbent foams. For example, by applying wave treatment during compression of dry super absorbent foams in order to get it in the form of thin pliable sheets convenient for practical applications, involves additional breakage of partitions between pores of the porous superabsorbent foam, thus favoring formation of a more extensively branched system of interconnecting pores.

It is yet another object of the present invention to provide apparatus for producing superabsorbent foams operating to expose the entire reaction mixture to the application of mechanical waves.

According to yet another aspect of the present invention, the method for producing porous superabsorbent foams may also include, apart of or instead of mechanical waves application, the alternation of pressure in the reaction volume of the formed reaction mixture by means of introducing into it a blowing agent under alternating pressure values.

According to the present invention, the application of mechanical waves is not limited to any class of compounds which form the polymeric foam through different mechanisms (e.g., polymerization, gelling, cross-linking, sintering).

There is thus provided, in accordance with a preferred embodiment of the present invention, a method for producing a superabsorbent foam including forming a reaction mixture comprising at least one compound capable of forming a superabsorbent foam, stirring the reaction mixture, applying mechanical waves to the reaction mixture and repeating the stirring and applying a selected number of times thereby forming the superabsorbent foam.

Furthermore, in accordance with a preferred embodiment of the present invention, the compound is collagen.

Furthermore, in accordance with another preferred embodiment of the present invention, the superabsorbent foam has a high absorption capacity to protein solutions.

Furthermore, in accordance with yet another preferred embodiment of the present invention, the reaction mixture includes a natural polymer.

Furthermore, in accordance with still another preferred embodiment of the present invention, the reaction mixture includes a synthetic polymer.

Furthermore, in accordance with an additional preferred embodiment of the present invention, the reaction mixture the compound is a monomer capable of being polymerized.

Yet further, in accordance with an additional preferred embodiment of the present invention, the compound is acrylic acid.

Furthermore, in accordance with a preferred embodiment of the present invention, applying mechanical waves includes sonicating and the waves are ultrasonic waves. Additionally, it includes sonicating the reaction mixture and the additional mechanical and ultrasonic wave treatments.

Furthermore, in accordance with another preferred embodiment of the present invention, the method further includes alternating the pressure of the reaction mixture during the step of repeating and applying additional mechanical waves to the formed superabsorbent foam thereby increasing its absorbing capacity.

Furthermore, in accordance with a preferred embodiment of the present invention, the method further includes compressing the superabsorbent foam, thereby increasing its absorbing capacity and reducing its volume.

Furthermore, in accordance with a preferred embodiment of the present invention, alternating includes employing a blowing agent under alternating pressure values.

Furthermore, in accordance with a preferred embodiment of the present invention, the method further includes drying the superabsorbent foam and sonicating the dry superabsorbent foam thereby increasing its absorbing capacity.

Furthermore, in accordance with yet another preferred embodiment of the present invention, applying includes applying non-linear mechanical waves to the reaction mixture.

Yet, in accordance with still another preferred embodiment of the present invention the non-linear mechanical waves are shock-waves.

Furthermore, in accordance with still another preferred embodiment of the present invention applying further includes applying physical energy to the reaction mixture, the physical energy can be ultraviolet light, visible light, ionizing radiation, microwave radiation or any combination thereof.

In addition, in accordance with a preferred embodiment of the present invention, there is provided the superabsorbent foam produced by the method described hereinabove.

In addition, in accordance with a preferred embodiment of the present invention, there is provided apparatus for forming a porous superabsorbent foam which includes a reactor having a reaction chamber therein for receiving a reaction mixture which includes at least one compound capable of forming a superabsorbent foam, a stirring unit for stirring the reaction mixture, means for applying mechanical waves to the reaction mixture and a control unit for repeating the operation of the stirring unit and the means for applying mechanical waves a selected number of times thereby forming the superabsorbent foam.

Furthermore, in accordance with a preferred embodiment of the present invention, the stirring unit includes a shaft and at least one blade operating to stir the reaction mixture in the reaction chamber.

Furthermore, in accordance with a preferred embodiment of the present invention, the apparatus further includes a receiving chamber for receiving the formed superabsorbent foam.

Furthermore, in accordance with a preferred embodiment of the present invention, the apparatus includes a first piston assembly having at least one piston for displacing the formed porous superabsorbent foam from a first position within the reactor to a second position within the receiving chamber.

Furthermore, in accordance with a preferred embodiment of the present invention, the piston and the blade are complementary in shape, thereby enabling the piston to displace the formed porous superabsorbent foam.

Furthermore, in accordance with a preferred embodiment of the present invention, the apparatus further includes a second piston assembly for displacing the formed porous superabsorbent foam from the receiving chamber to a collection chamber.

Furthermore, in accordance with a preferred embodiment of the present invention, the first piston assembly and the second piston assembly operate at least partly in the same volume.

Furthermore, in accordance with a preferred embodiment of the present invention, the apparatus further includes means for changing the pressure in the reaction chamber and for introducing a blowing agent into the reaction mixture.

Furthermore, in accordance with a preferred embodiment of the present invention, the apparatus further includes means for applying physical energy into the reaction mixture.

Furthermore, in accordance with another preferred embodiment of the present invention, the physical energy can be ultraviolet light, visible light, ionizing radiation, microwave radiation or any combination thereof.

Furthermore, in accordance with another preferred embodiment of the present invention, the stirring unit of the apparatus includes at least one movable blade to oscillate the reaction mixture and a blade oscillating mechanism.

Furthermore, in accordance with another preferred embodiment of the present invention, the blade includes a frame, at least one movable blade section operating to rotate within the frame and a blade-section rotating mechanism.

Furthermore, in accordance with another preferred embodiment of the present invention, The apparatus includes means for applying physical energy to the reaction mixture. The physical energy can be ultraviolet light, visible light, ionizing radiation, microwave radiation or any combination thereof.

Furthermore, in accordance with another preferred embodiment of the present invention, The means for applying mechanical waves are means for applying non-linear mechanical waves such as shock-waves to the reaction mixture.

There is therefore provided, in accordance with another preferred embodiment of the present invention, a porous superabsorbent foam substantially made of polyacrylate.

Finally, in accordance with a preferred embodiment of the present invention, a porous superabsorbent foam substantially including collagen is provided.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
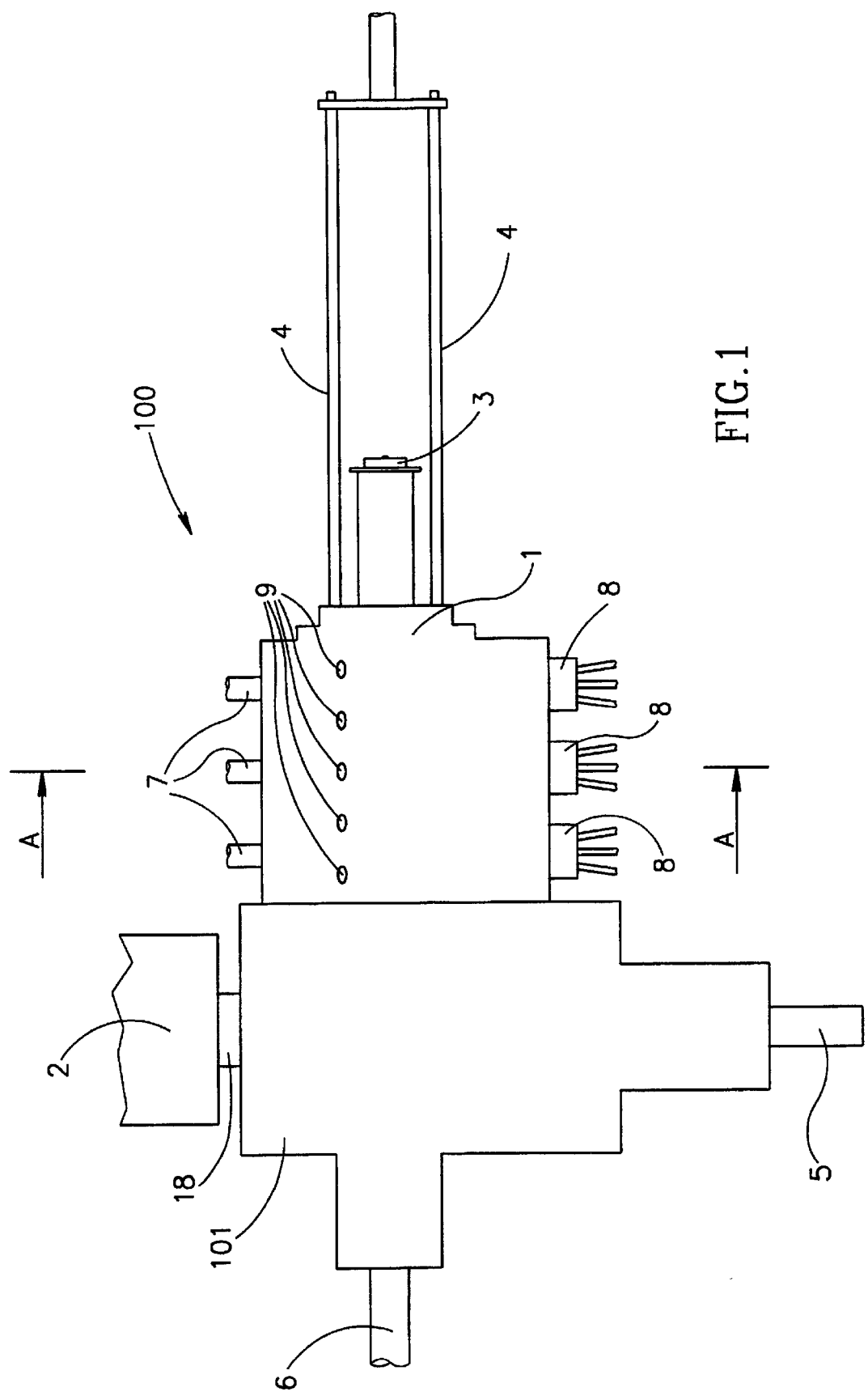
FIG. 1 is a schematic top view illustration of apparatus for producing porous superabsorbent foams, constructed according to a preferred embodiment of the present invention.
Figure 2:
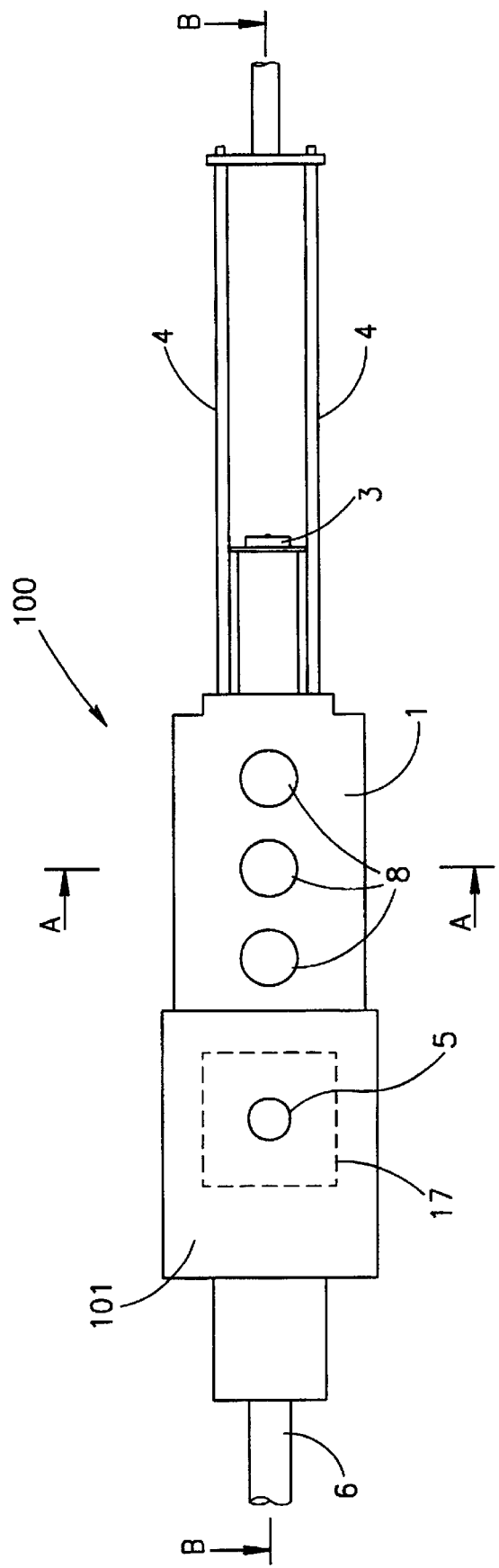
FIG. 2 is a schematic side view illustration of the apparatus of FIG. 1.
Figure 3:
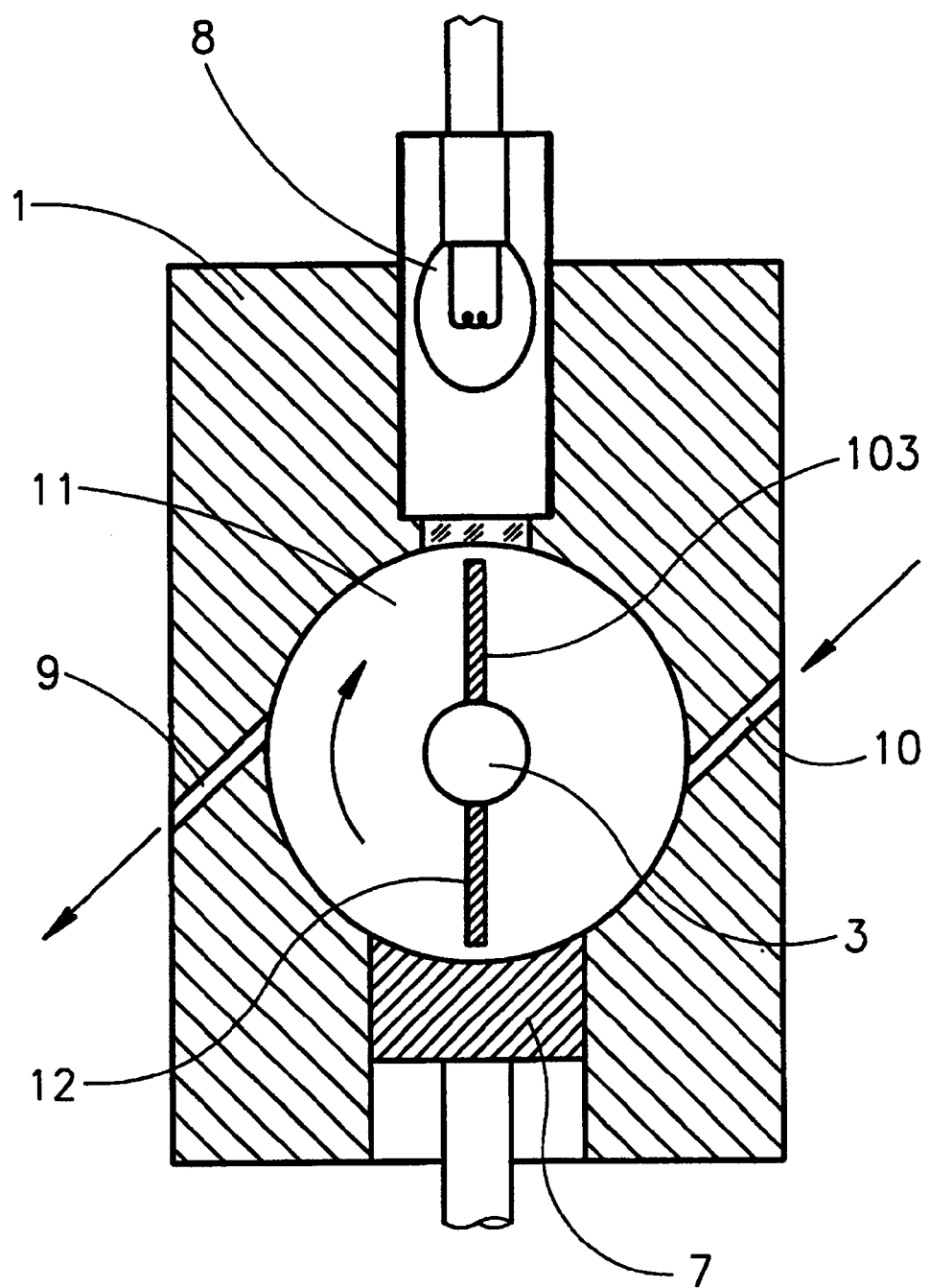
FIG. 3 is a cross sectional schematic view of the apparatus of FIGS. 1 and 2 along lines A—A.
Figure 4:
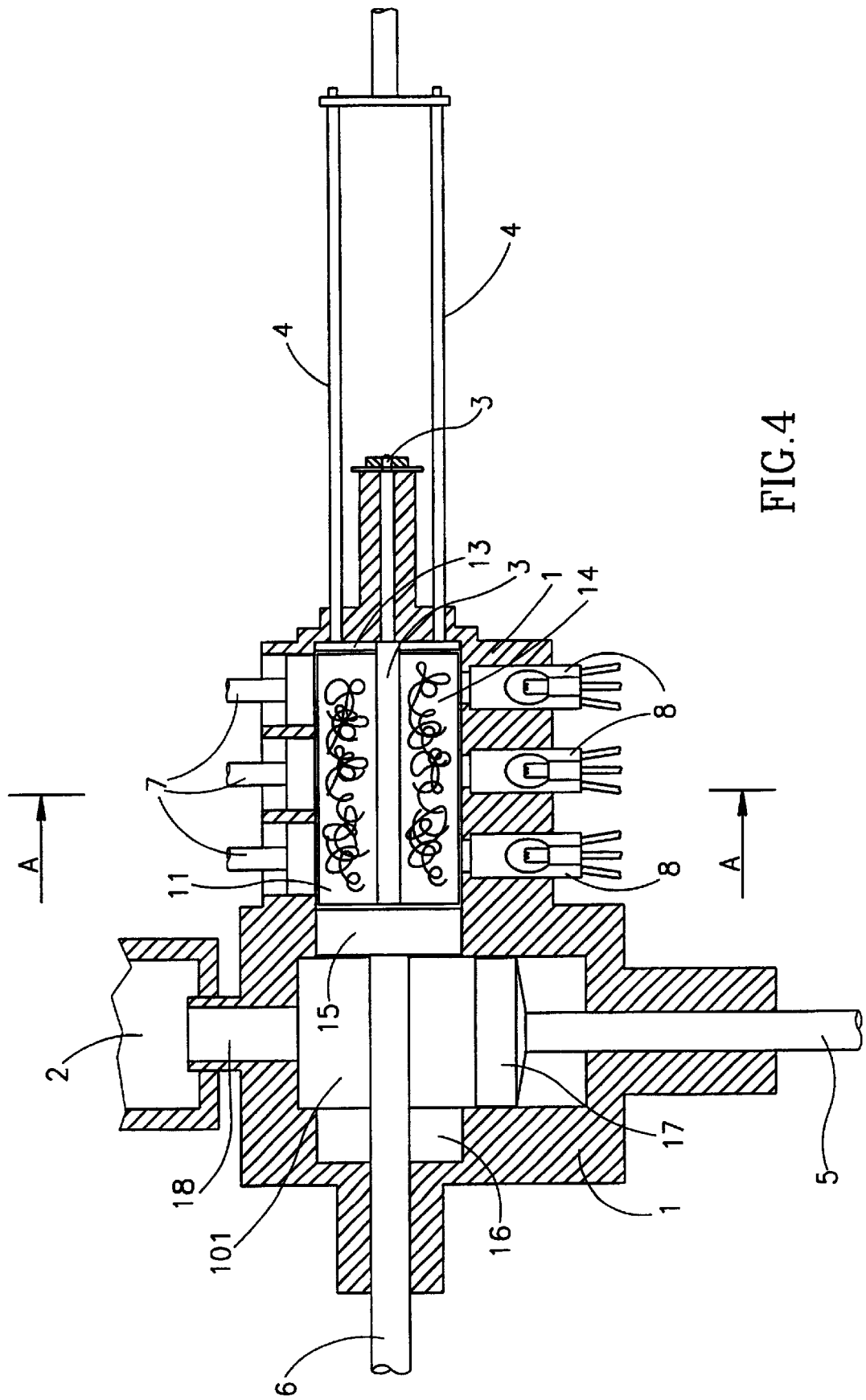
FIGS. 4, 5 and 6 are schematic cross sectional illustrations along lines B—B of FIG. 2 illustrating the apparatus of FIGS. 1–3 in three working positions.
Figure 5:
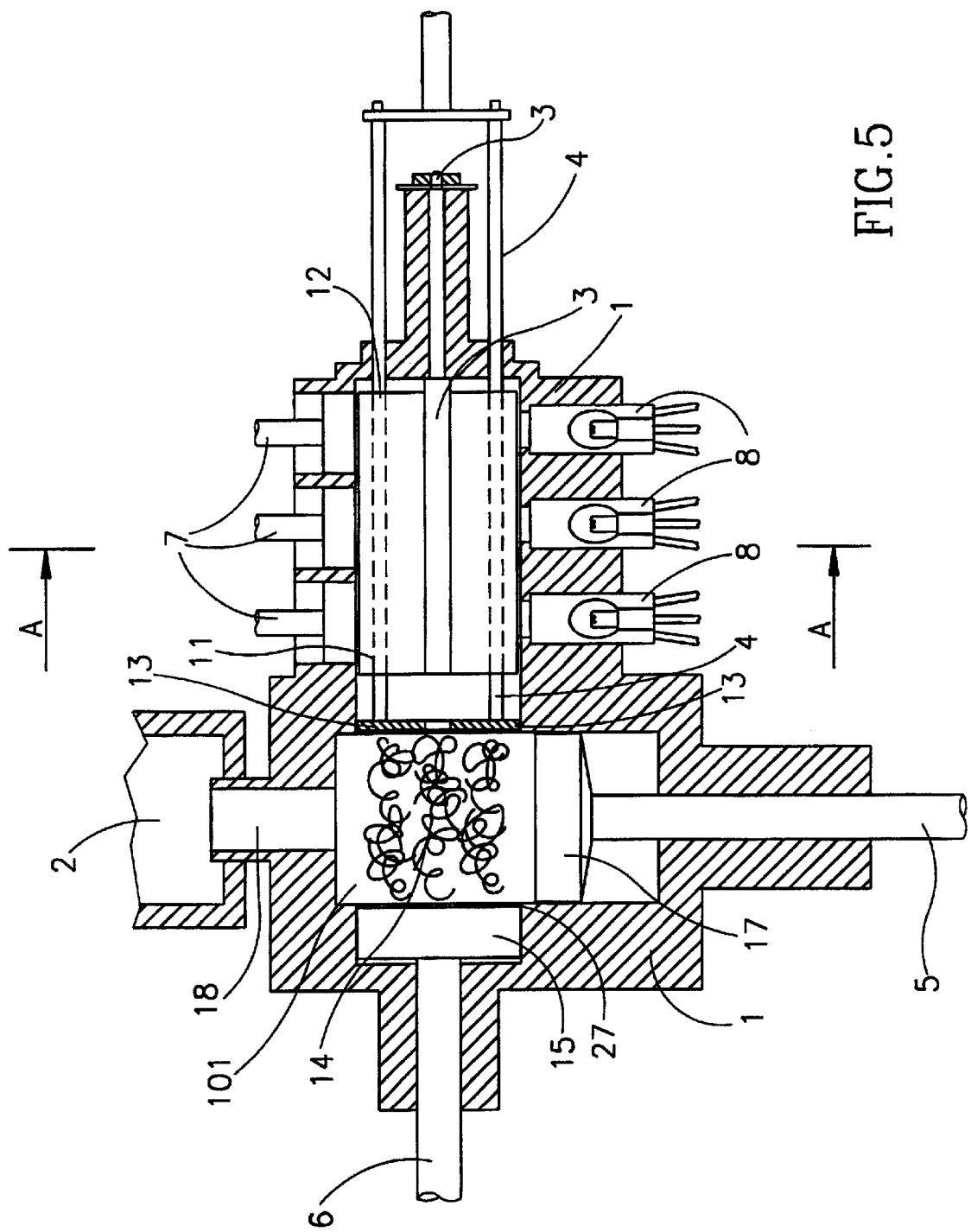
Figure 6:
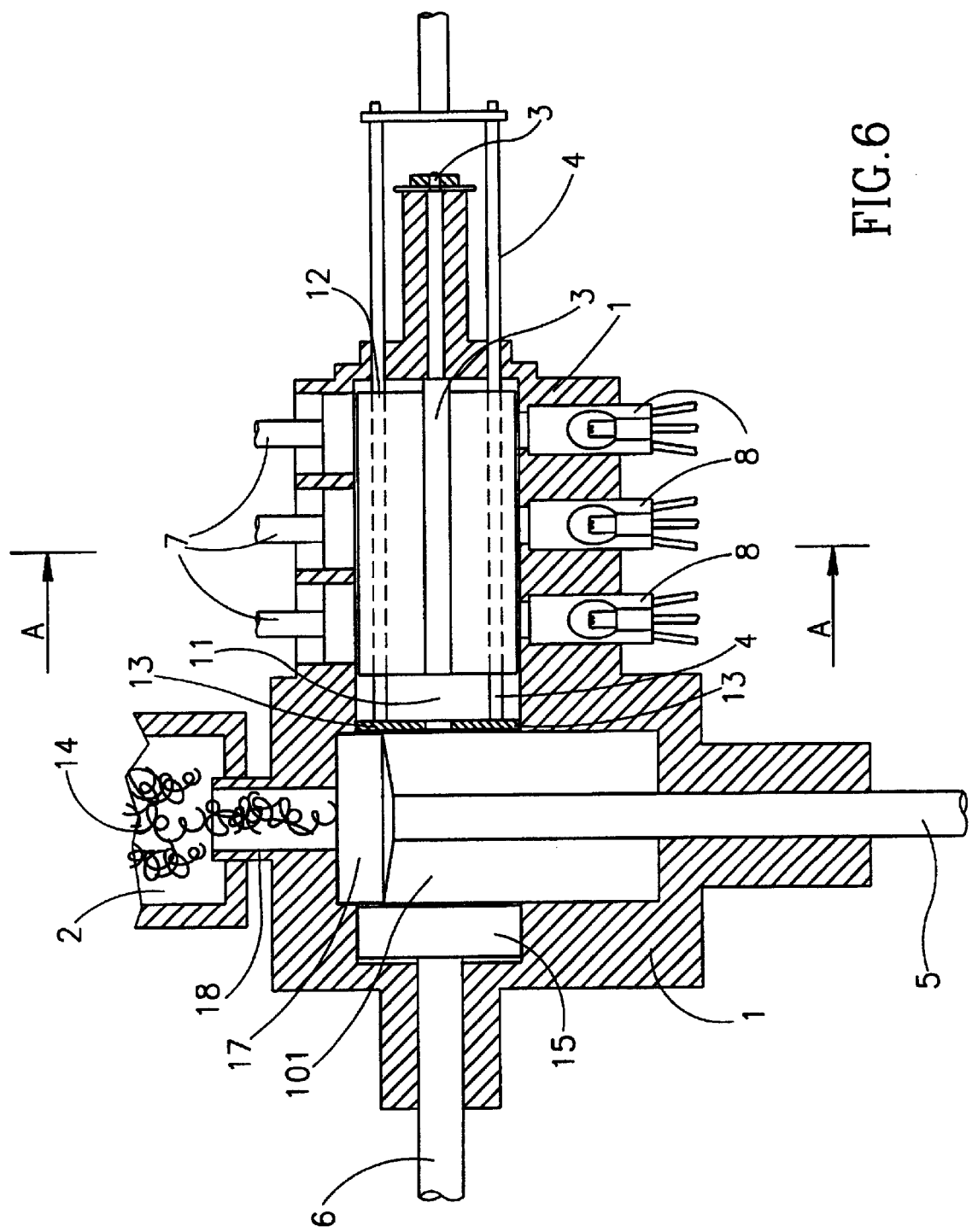

Reference is now made to FIGS. 1–6. FIGS. 1–3 schematically illustrate the apparatus for producing the superabsorbent foam of the present invention. FIGS. 4–6 are schematic cross-sectional illustrations of the apparatus in a first, second and third working positions, respectively.

It is noted that, for a better understanding, like components are designated by like reference numerals throughout the various figures.

The apparatus, generally referenced 100, comprises a reactor 1 having a reaction volume 11 (FIG. 3) defined by two pistons 13 and 15 in a first working position (FIG. 4). In the reaction volume 11, the porous superabsorbent foam is formed from a suitable reaction mixture.

The apparatus 100 also comprises a receiving chamber 101 for receiving the superabsorbent foam after its production in reactor 1. The superabsorbent foam is then pushed out of receiving chamber 101, through outlet 18, into a collection chamber 2, for further processing.

In accordance with a preferred embodiment of the present invention, the reactor 1 and the receiving chamber 101 are generally perpendicular.

As best seen in FIG. 3, a stirring unit 103 is operative within the reaction volume 11 to rotate and stir the reaction mixture 14 (FIG. 4) from which the porous superabsorbent foam is formed. Stirring unit 103 comprises a shaft 3 and stirring blades, generally designated 12.

As best seen in FIG. 41 apparatus 100 also comprises a piston assembly which includes a first piston arrangement, comprising at least one piston 13 operated by a connecting shaft 4 and a second piston arrangement, comprising a second piston 15 moved by a connecting shaft 6. The first piston 13 and the second piston 15 define the reaction volume 11 within the reactor 1 and operate to displace the formed superabsorbent foam from its first location in the reaction volume 11 (FIG. 4) to a second location in the receiving chamber 101 (FIG. 5). A third piston arrangement comprises a shaft 5 which is operative to move a piston 17 within the receiving chamber 101, for displacing the formed superabsorbent foam from its second location in the receiving chamber 101, via outlet 18, to a collection chamber 2 (FIG. 6).

An object of the present invention is to apply mechanical waves to the reaction mixture, thereby forming the porous superabsorbent foam. According to a preferred embodiment of the present invention, there is provided a source of sonication energy which operates to apply ultrasound and audible waves of a desired wavelength, amplitude and shape to the reaction mixture. The source of sonication energy may include a transducer 7 molded to the wall of the reactor 1 and forming part thereof, or any other suitable element for providing sonication energy known in the art, as described for example in *"Practical Sonochemistry"* by Timothy J. Mason, published by Ellis Hormood Ltd. in 1991, in particular in section 4.3 thereof.

Apparatus 100 also comprises a plurality of Ultra Violet (UV) light sources 8 which operate to apply UV light to the reaction mixture in order to induce cross linking reactions therein. According to a preferred embodiment of the present invention, the superabsorbent foam is a collagen based solution capable of forming cross links therebetween. The application of UV energy may be useful in medical application where due to potential unfavorable action of cross linking reagents they are not useable due to their potential health risk, i.e. their unfavorable crosslinking with the body tissues.

Apparatus 100 also comprises a plurality of openings 9 and 10 (FIG. 3) forming channels in the wall of the reactor 1. The openings 9 and 10 operate as inlets and/or outlets for a blowing agent. The blowing agent is preferably a suitable inorganic gas such as, air, nitrogen and carbon dioxide; or an organic gas or volatile liquids, such as aliphatic hydrocarbons, preferably having up to seven carbon atoms in their chain and, halogenated aliphatic hydrocarbons, preferably fluorinated hydrocarbons with up to four carbons in their chains. The blowing agent is introduced into the reactor 1 by any suitable system capable of increasing and decreasing pressure in the reaction volume 11. For example, the blowing agent may be stored outside the reactor, under pressure in a tank having a system of tubes and cocks (not shown). By periodically and synchronously opening and closing the cocks, pressure pulses are generated within the reaction volume 11, thereby causing multiple disruptions of the foam cells walls and formation of an extensively branched porous system in the solidifying foam which leads to improved absorbing qualities.

As best seen in FIG. 3, the openings 9 and 10 are preferably oblique with respect to that of the blades 12 so as to minimize leakage of foam with the blowing agent from the reactor chamber 11.

Reference is now specifically made to FIGS. 4–6, which illustrate the apparatus 100 in three different operating positions.

In the first position (FIG. 4), piston 13 and piston 15 define the reaction volume 11 wherein the solidification of the reaction mixture 14 takes place.

In the second position (FIG. 5), after formation of the foam from the reaction mixture 14, piston 15 is recessed into its housing 27 allowing piston 13 to push the foam formed from the reaction mixture 14 into receiving chamber 101. Housing 27 is configured to allow piston 15 to be recessed, thereby enabling piston 17 to move freely within the receiving chamber 101 so as to force the foam formed from the reaction mixture 14 through outlet 18 into the collection chamber 2.

It is a particular feature of the present invention that pistons 15 and 17 is operate substantially within the same volume. Thus, the formed superabsorbent foam may be displaced, within the reactor 1, with a minimum of compression deformation, thereby, preserving the porous structure of the solidified superabsorbent foam formed from the reaction mixture 14.

Reference is now made to FIGS. 7–10 which illustrate four alternative stirring units 103 of the apparatus 100. According to a preferred embodiment of the present invention, the shape of the stirring unit 103 complements the shape of piston 13 so as to enable displacement of piston 13 in the reactor 1.

Figure 7:
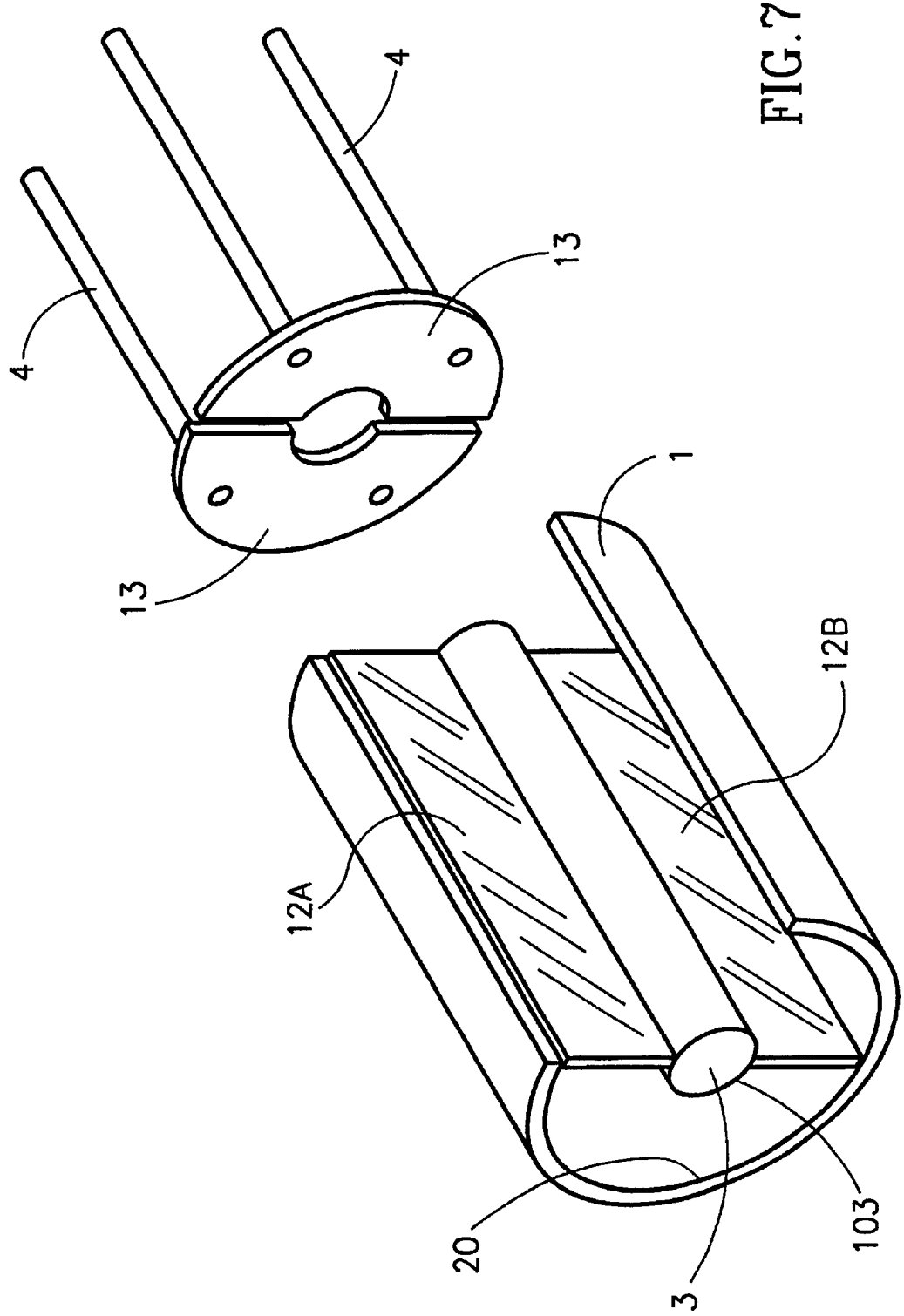
FIGS. 7, 8, 9 and 10 are schematic isometric illustrations of four alternative embodiments of blades employed in the stirring unit of the apparatus of FIGS. 1–3.

FIG. 7 illustrates two planar blades 12a and 12b, each blade having one edge fixed to the cylindrical shaft 3 while the other edge is in close proximity to the reactor wall 20. The sources applying mechanical waves to the reaction mixture 14, such as transducers 7, are located adjacent to the reactor wall 20 so as to increase the efficiency and formation of pores in the reaction mixture 14. In a cylindrical reactor, the rotation of the blades 12 distributes the applied waves throughout the formed foam and effectively transfers the foam between the area in the vicinity of the reactor wall 20 and the rest of the reactor area.

Figure 8:
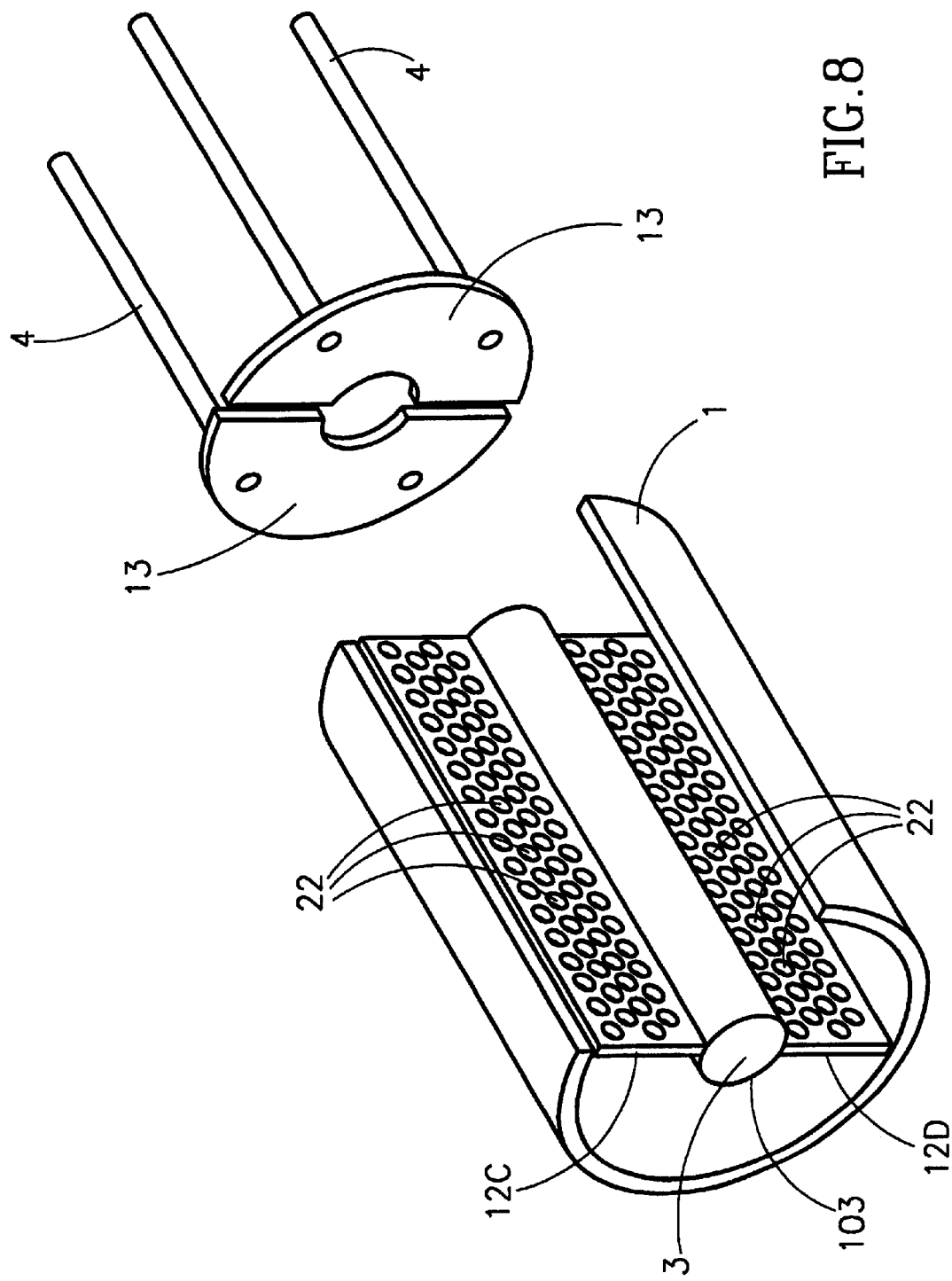
Figure 9:
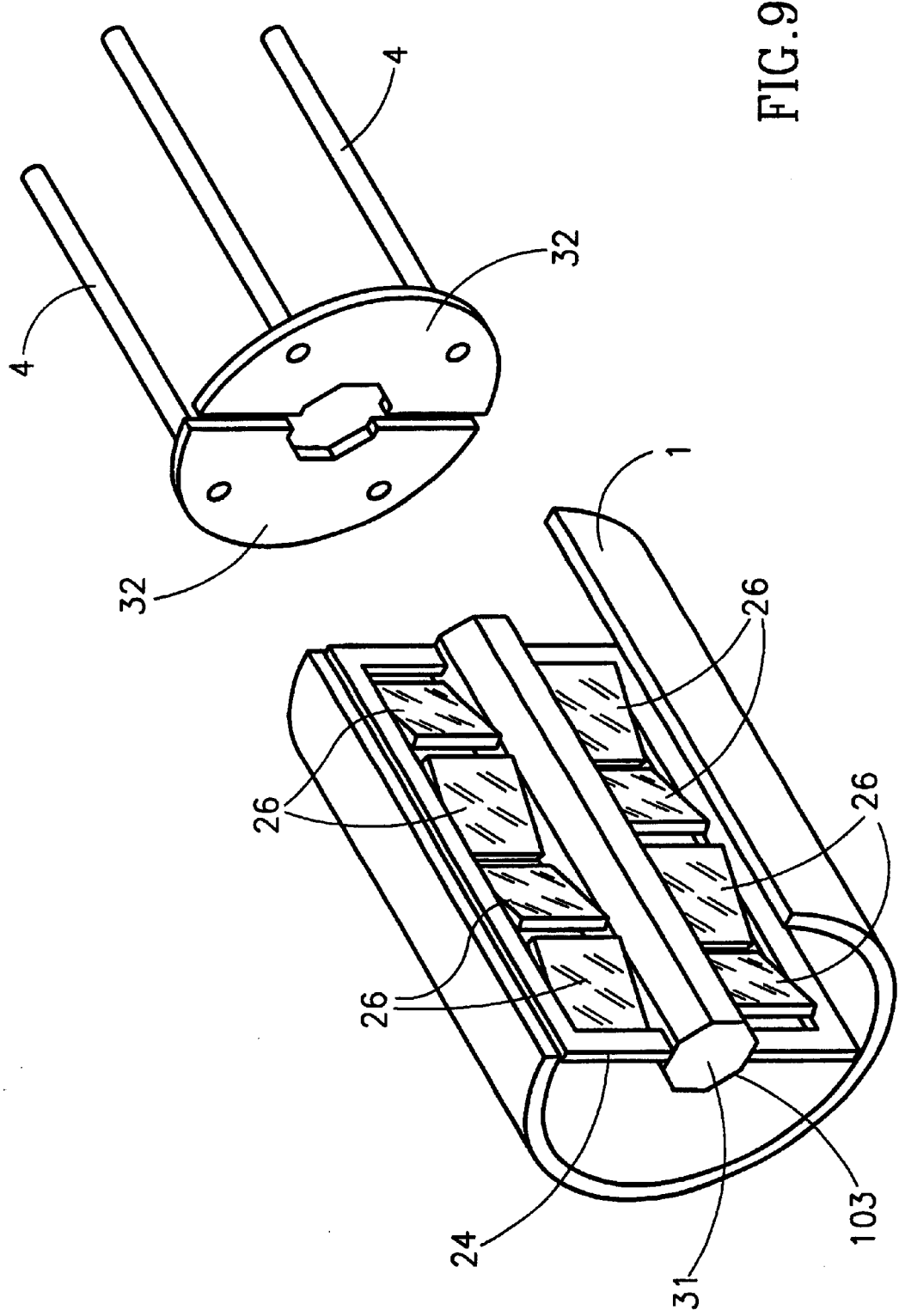
Figure 10:
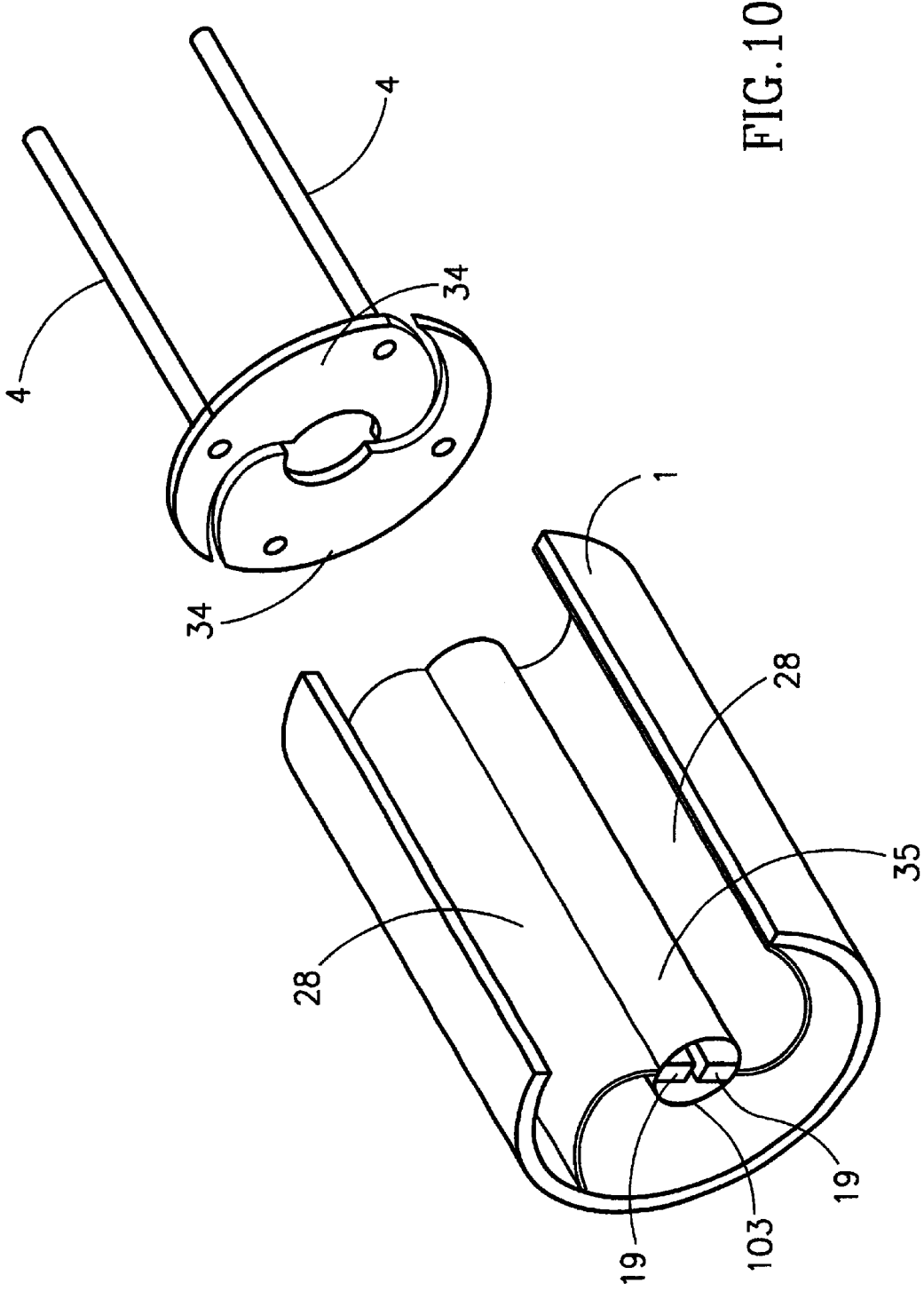

FIGS. 8–10 illustrate alternative stirring units for the capable and efficient transfer of foam within the reaction volume 11.

In the embodiment of FIG. 8, the blades 12c and 12d have multiple openings 22 arranged therethrough in a staggered fashion. As described with respect to FIG. 7 hereinabove, the increased turbulence and vortexing caused by the rapid rotation of the blades transfers wave motion throughout the foam.

FIGS. 9 and 10 illustrate another two preferred embodiments of the stirring unit 103. The stirring unit of FIG. 9 comprises a frame 24 having mounted therein a plurality of movable blade sections 26 on each side of the central shaft 31. Each of the blade sections 26 is capable of independently rotating around an axis coinciding with the plane of the frame 24. Preferably, the blade sections 26 are configured in a zig-zag like configuration as shown in FIG. 9.

In the illustrated embodiment of FIG. 9, the shaft 31 on which the blade sections 26 are mounted is of hexagonal form to enable rotation of blade sections 26 about a planar surface. On completion of the reaction cycle and solidification of the foam, the blade sections 26 can be retracted within the plane of the frame 24, so as not to interfere with the movement of the pistons 32. The solidified foam can then be easily displaced by pistons 32 and expelled from reaction chamber 11 into receiver chamber 101.

The blade sections 26 can be rotated by any suitable mechanism, such as a cam arrangement in which the rod-like protrusions of the blade sections 26 within the hollow interior of the shaft 31 (not shown) serve as cam-operated driven members.

FIG. 10 shows a stirrer device with curved blades 28. The curvature of the blades is characterized in that the angle between the curved blade surface and a plane, parallel to a tangent plane to the cylindrical shaft 35 at the line of blade fixing, continuously decreases from 90 degrees at the shaft surface to about 5–10 degrees near the side wall of the reaction chamber.

In order to prevent congregation of congealed foam fractions, which are continuously formed and accumulated near the wall of reactor 1 in the course of foam solidification, and to provide more uniform action of physical energy on the reactor content, the near-wall layers are periodically disturbed by oscillations of the blades provided with a system of coils 19, placed in the interior of the hollow shaft 35, as shown in FIG. 10, and connected with the rod-like protrusions of the blades 28 into the shaft interior.

It will be appreciated that this type of blade curvature affords a differential rate of transfer of the contents from the center of the reactor to areas on the periphery, proximal to the transducers 7. The closer the contents are to the center of the reactor, the more efficiently they are transferred to the reactor's side wall.

It will be appreciated that the apparatus 100 has numerous advantages for forming superabsorbent foams, a few of which are described hereinbelow.

The apparatus 100 provides efficient exposure of the reaction mixture to different kinds of physical energy including those whose propagation in non-homogeneous media is deficient since the content of the reaction mixture is transferred by the stirring unit from the center of the reaction volume 11 to its periphery where the wave sources are located.

Moreover, the apparatus 100 is characterized by the efficient mass transfer within the reactor 1, of the reactor contents, having a wide range of viscosity values up to solidification and including mixtures whose viscosity increases during the reaction.

Additionally, the apparatus 100 enables the use of external and/or internal blowing agents and the possibility of inducing pressure pulses of blowing agent within the reaction volume.

The apparatus 100 provides efficient extrusion of the solidified superabsorbent foam from the reaction volume 11 to the receiving volume 101 and the collection volume 2 while substantially preserving the porous structure of the solidified foam.

One of the preferred compounds for forming the superabsorbent foam of the present invention is collagen. The swelling rate of crosslinked collagen in water depends on its crosslinks density, the lower the density (which is determined by the crosslinker concentration) the higher the swelling rate (WAC). A set of collagen samples with different crosslinks densities were prepared and the effect of a physical treatment on collagen samples with different values of basic absorption capacity was studied. Collagen was crosslinked with glutaraldehyde (GA). Collagen-GA systems were gelled within a time frame of 2–20 min (depending primarily on GA concentration). These time intervals were convenient for exposing the reaction mixtures to physical factors leading to solidification in the course of the reaction.

The preferred method for preparing natural and synthetic polymer based superabsorbent foams comprises the application of ultrasound and/or audible waves to the reaction mixture with or without additional wave application, pressure alternation and compression as described in more detail hereinbelow.

The following examples illustrate without limitation certain aspects of the present invention.

EXAMPLE 1

This example illustrates the effect of sonication of a reaction mixture on absorption properties of loosely crosslinked collagen samples.

Experimental Conditions

Experiments were conducted using a conventional laboratory Branson sonifier-450 as a source of vibrational energy and collagen crosslinked with glutaraldehyde (GA) as a test-reaction mixture.

A Branson sonifier 450 provides a constant oscillation frequency of 20 Khz. A horn with a ½" probe was used. At the end of the probe a stainless steel disc (diameter 35 mm, thickness 1 mm) was mounted. The reaction mixture (about 25 ml) was introduced into a cylindrical vessel with a plane bottom (internal diameter 50 mm) with a magnet rod therein for stirring. A disc at the end of the sonifier probe was placed at the reaction mixture/air interface so as to imitate the sonification of the reaction mixture as described with respect to the preferred embodiment of the invention.

An intermittent sonication scheme was used, that is, stirring and sonication were switched on in turn, for periods of 10 seconds at a time. Sonication caused formation of a fluffy fine-cell foam from the reaction mixture containing surfactants (described hereinbelow).

The foam was progressively solidified in the course of the reaction according to development of the crosslinking process. The intermittent sonication-stirring treatment was continued until the foam has been solidified to such an extent that its porous structure was preserved on subsequent storage at room temperature for the further development of crosslinking process. This solidification time was about 4–5 min for the reaction mixture used, the composition of which is described hereinbelow) and GA concentration 0.30% v/v (loosely crosslinked collagen samples).

Temperature of the reaction mixture was controlled with a thermocouple facility and did not exceed 42–45° C. due to using the intermittent sonication and pulsed mode scheme (duty cycle 40% at output control of 4–5).

Composition of the Reaction Mixture.

The reaction mixture contained a water-soluble collagen (Serva, Heidelberg, Germany) as a major component and some amount of gelatin (Mata Food Industries, Hadera, Israel). Other chemicals were from Sigma Chem. Co (St. Louis, USA). Additives which were used in the reaction mixture included the surfactants cationic benzalkonium chloride (known as an efficient disinfectant) and non-ionic Tween-20 (widely used for pharmaceutical applications). Glycerol was used as a plasticizer, and phosphates and sodium chloride for buffering and isotonicity.

The reaction mixture used in Example 1 was made in a following way: Initially 7% (w/v) stock solutions of collagen, gelatin, Tween 20 and glycerol, each in 0.2% solution of benzalkonium chloride in phosphate-buffered saline, Ph 7.4 (BC/PBS), were prepared. Then the stock solutions were mixed in the following proportion: 15 ml of collagen, 5 ml of gelatin, 1.25 ml of Tween 20 and 1.25 ml of glycerol and 2.5 ml of BC/PBS to provide a total volume of the reaction mixture of 25 ml.

Preparation of Samples 25 ml of prepared reaction mixture were placed in a reaction vessel, as described hereinabove with respect to the preferred embodiment of FIGS. 1–10, a magnetic stirrer was switched on and 2.78 ml of 3% of water solution of GA was added to the reaction mixture to give final concentration of GA in the reaction mixture of 0.30% and the intermittent stirring-sonication treatment was performed according to the scheme given above until the foam was solidified to a required consistency. After treatment the foam was stored for an hour at room temperature to allow further development of collagen and gelatin crosslinking. Then, the foam was placed into a vacuum oven at 40° C. for drying overnight. The reference non-sonicated samples were prepared in the same way and in the same vessel except the sonifier was not switched on.

Measurement of Swelling Rates (WAC)

It is noted that, while the term WAC is used throughout this application to represent the measured swelling rate of tested samples, this term is used to express the capacity to absorb all fluids whose absorbance was tested such as PBS and water and is not limited to water only. The specific fluid used for measuring the WAC values is indicated for each of the Examples hereinbelow.

A dry sample was carefully weighed (dry weight) and then placed into a vessel with PBS in a thermostated bath at 37° C. for certain time intervals. At the end of each time interval the sample was removed from PBS, blotted gently with filter paper to remove excess of PBS on the sample surface and weighed (wet weight). The difference between the wet and dry weights gives the amount of water absorbed by the sample. The water absorption capacity of the sample was expressed as amount of grams of water absorbed per gram of dry sample.

Figure 11:
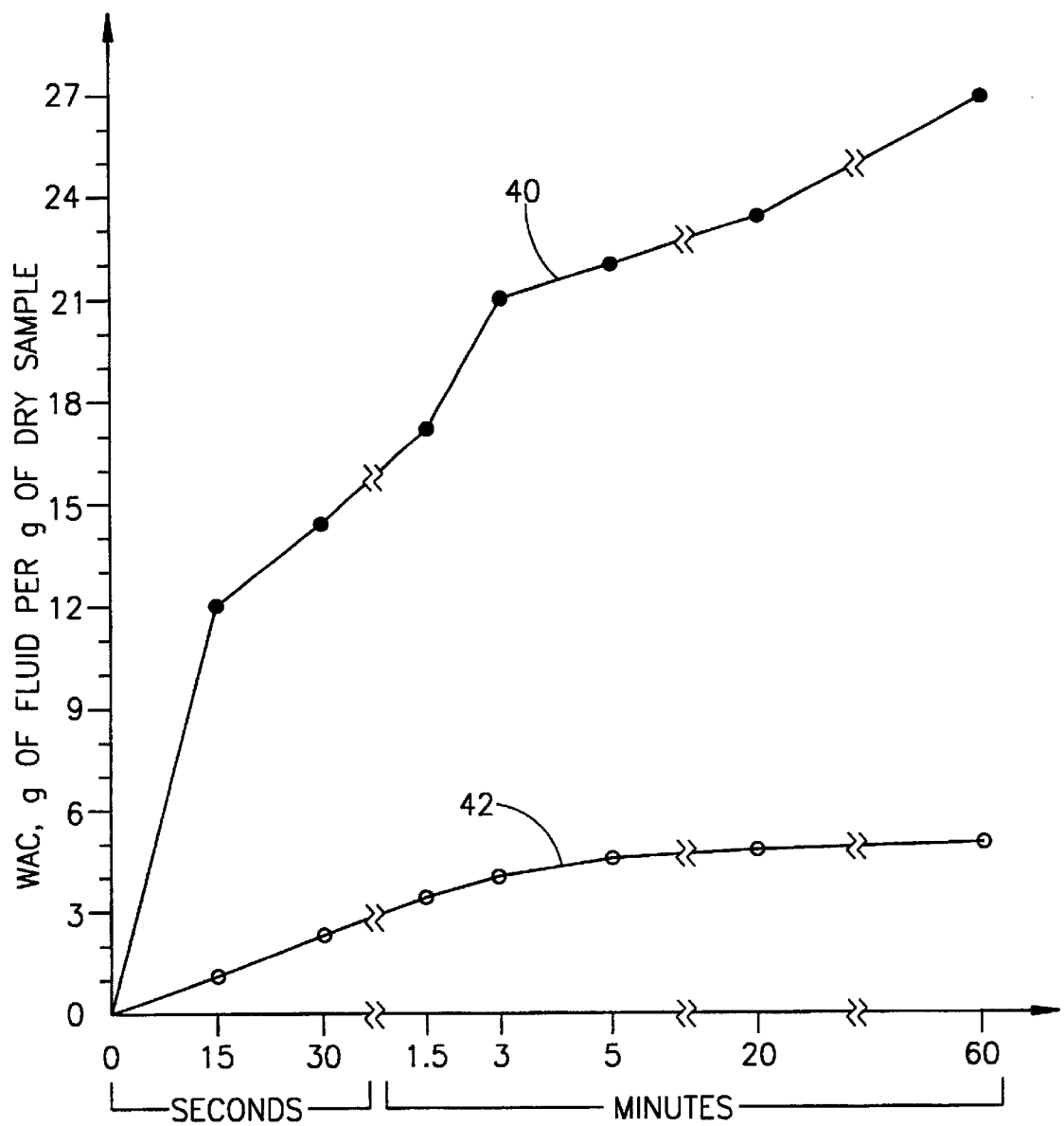
FIG. 11 is a graph illustrating the improved water-absorbent capacity (WAC) of a collagen foam of the present invention, in three different time ranges of swelling.

Reference is now made to FIG. 11, which is a graph illustrating WAC, i.e., the swelling capacity (Y-axis) of the superabsorbent foam of the present invention (curve 40) compared with that of prior art conventional collagen sample (curve 42) for three time ranges (X-axis). Swelling rates of loosely crosslinked (0.30% of GA) collagen samples were prepared by using sonication treatment. The effect is illustrated in curve 40. A conventional collagen sample, that is without sonication is illustrated in curve 42. The time scale covers intervals (from seconds to 60 minutes).

As clearly seen in FIG. 11 the swelling of the loosely crosslinked collagen samples prepared in accordance with the method of the present invention employing sonication (curve 40) is higher in all time ranges than the WAC of the same collagen without wave application (curve 42). It is clearly seen that the swelling of the porous superabsorbent foam of the present invention is superior both at shorter and longer times.

The following examples illustrate the preparation of superabsorbent foam. Collagen was used as the example in the experiments. These illustrations are by way of example only and are not to be construed as in any way limiting to the present application.

More specifically, the sonicated sample swells faster and more than the non-sonicated sample. The difference is particularly large at the initial stage of swelling (more than 9 times higher as compared with the non-sonicated sample within first 15 seconds). After an hour of swelling, the sonicated sample exceeds the non-sonicated sample by a factor of about 5.5 and its WAC reaches as much as 27 grams of absorbed water per 1 gram of dry sample.

EXAMPLE 2

Effect of Sonication of a Reaction Mixture on Absorption Properties of Strongly Crosslinked Collagen Samples Strongly crosslinked collagen samples (sonicated and non-sonicated) were prepared in the same way as the loosely crosslinked samples as described in Example 1, except that a much larger GA concentration of 1.75%, instead of 0.35%, was used. Strongly crosslinked samples absorb significantly less water than loosely crosslinked samples. However in this case sonication of the reaction mixture also markedly increases swelling rates (Table 1).

TABLE 1

Swelling rates (grams of water per gram of dry sample) of sonicated and non-sonicated strongly crosslinked collagen samples at different swelling times

| Sample | Swelling time | | |
|---|---|---|---|
| | 1 min | 5 min | 1 hour |
| Sonicated | 1.71 | 3.98 | 4.62 |
| non-sonicated | 0.31 | 0.90 | 1.25 |

Swelling rates of sonicated samples exceed those of the non-sonicated samples by a factor of 5.5 after 1 min and by factors more than 3.5 after 5 min and 1 hour.

EXAMPLE 3

Swelling of Sonicated and Non-sonicated Collagen Samples in a Protein Solution

Sonicated and non-sonicated collagen samples were prepared as in the Example 1, except the concentration of GA was 1% to cause moderate crosslinking. Swelling of samples was performed in 7% solution of bovine serum albumin in phosphate-buffered saline (PBS) and the values of swelling rates in albumin solution were compared with those in PBS without protein. The data obtained are presented in the Table 2.

TABLE 2

Swelling rates (grams of water per gram of dry sample) of sonicated and non-sonicated collagen samples in PBS and in 7% albumin solution in PBS

| Swelling media | Samples | Swelling time (min) | | |
|---|---|---|---|---|
| | | 2 | 5 | 15 |
| PBS | Sonicated | 5.02 | 6.43 | 7.36 |
| | non-sonicated | 0.76 | 1.48 | 1.82 |
| Albumin | Sonicated | 4.87 | 6.20 | 6.90 |
| | non-sonicated | 0.47 | 1.02 | 1.33 |

Table 2 shows that the swelling rates of the sonicated samples in a concentrated protein solution of 7% albumin are only slightly decreased (by about 3–5%) as compared with the PBS while those for non-sonicated samples are decreased by 25–40%.

It will be appreciated that 7% albumin solution was taken since its total protein content approximately corresponds to blood serum and wound exudates and thus provide an indication for the swelling in these important biological fluids. The ability of sonicated samples to swell readily in such protein solutions is important for some medical applications, e.g. for wound dressings.

EXAMPLE 4

Figure 12:
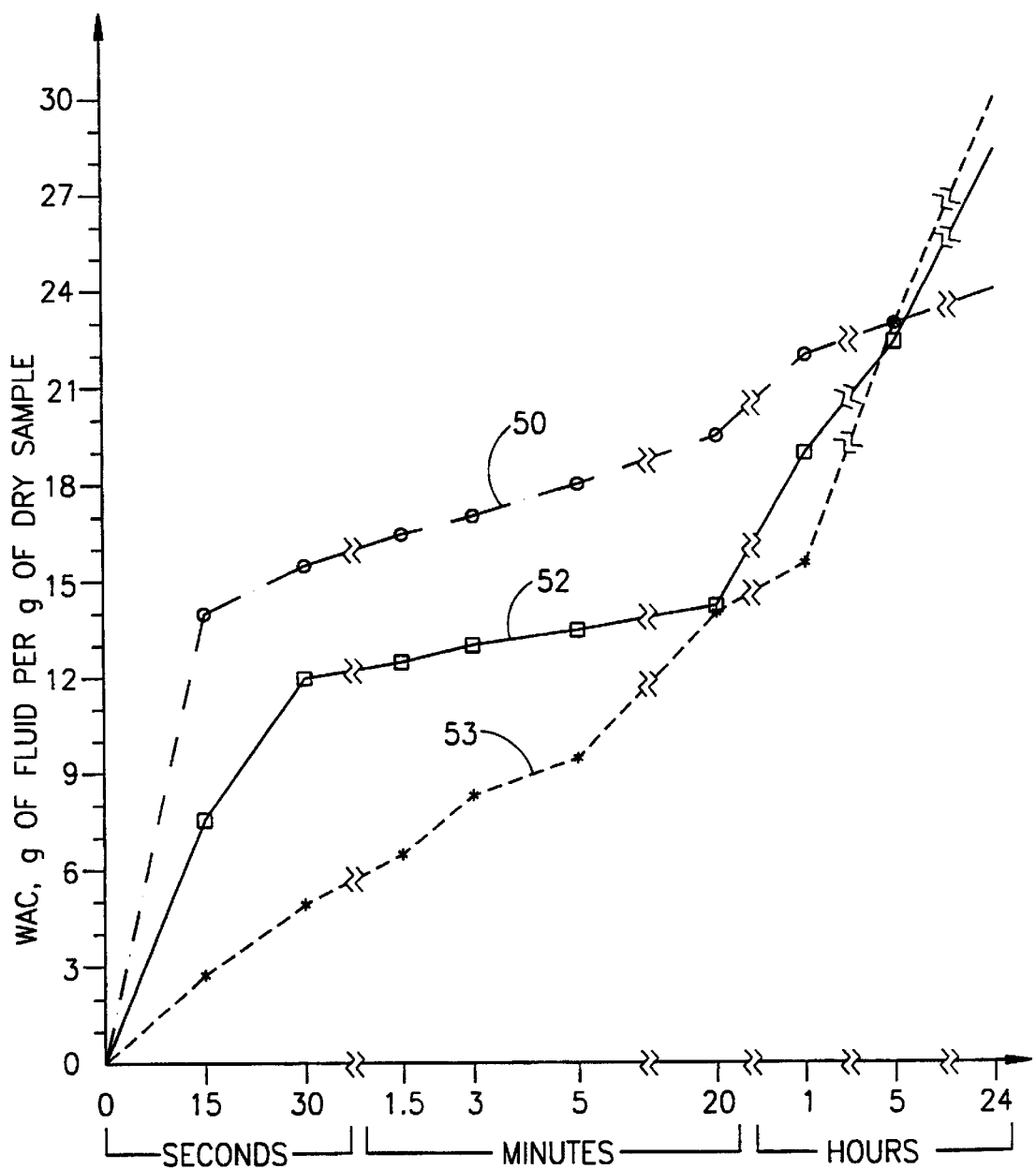
FIG. 12 is a graph illustrating the effect of compression of a collagen foam of the present invention on its WAC in different time ranges of swelling.

Effect of Compression of Dried Sonicated Collagen Samples on their Absorption Capacity This experiment was performed using loosely and strongly crosslinked collagen samples prepared in the same way as in Examples 1 and 2, respectively. After drying some samples were compressed under various pressure values in the range of 10–1000 Bar and swelling rates of compressed and non-compressed samples were estimated for different time intervals as presented in FIG. 12 to which reference is now made and Table 3 for loosely and strongly crosslinked collagen samples, respectively.

A distinct difference was observed between the compression effects on the swelling rate of loosely and strongly crosslinked collagen samples prepared by means of the proposed technology. As shown on FIG. 12, compression of loosely crosslinked sonicated sample under relatively small pressure of 15 Bar (curve 52) decreases the swelling rate during the first hour of contact with PBS but further, at 5 hours, the swelling rate of compressed sample reaches that of non-compressed one (curve 50) and at 24 hours exceeds it. This effect is more pronounced under stronger pressure of 150 Bar (curve 53 of FIG. 12). At still higher pressure values of about several hundred Bar swelling rates of loosely crosslinked samples are decreased at all time intervals (not shown).

However in the case of strongly crosslinked sonicated samples (Table 3) a strong compression under value pressure such high as 1,000 Bar markedly increases the swelling rate at all time intervals studied (from 15 seconds up to 24 hours). The effect is less pronounced at relatively small pressure of 30 Bar.

TABLE 3

Swelling rates (grams of water per gram of dry sample) of non-compressed (0 Bars) and compressed at 30 and 1000 Bars strongly crosslinked collagen samples

| Pressure | Swelling Time | | | |
|---|---|---|---|---|
| Bars | 15 sec | 3 min | 1 hour | 24 hours |
| 0 | 1.63 | 3.06 | 4.88 | 6.72 |
| 30 | 1.85 | 4.40 | 6.35 | 8.41 |
| 1,000 | 2.45 | 6.95 | 8.83 | 10.37 |

EXAMPLE 5

Effect of Additional Sonication of Dry Sonicated Samples on their Absorption Capacity This experiment was performed on moderately crosslinked sonicated collagen samples prepared in the same way as in the Example 1, except that the GA concentration was 1%. Instead of compression as in the Example 4, the dry samples were sonicated. This "dry" sonication was in addition to "wet" sonication of the reaction mixture occurring during the preparation of these samples. Therefore the sonication of dry samples is called here as "additional" sonication.

For this treatment the dry sample was placed in a metal cylinder having an internal diameter of 32 mm. On the end of the ½" sonifier probe a stainless steel disc 30 mm in diameter and 3 mm in thickness was mounted. The disc was introduced into the cylinder interior containing the sample through a compressible rubber layer. The rubber layer served as a thermo-isolation unit to avoid overheating of the sample. To provide transmission of the sonication energy to the sample through the rubber layer a pressure of 6 Bar was applied to the unit having the disc at its end.

Sonication was performed in a pulse mode (duty cycle 0.3). The sample was treated with 60 pulses in total with a 2 minutes interval between the runs of 10 pulses. Temperature of the sample was controlled with a thermocouple facility between the runs of the pulses did not exceed 45–48° C.

This treatment caused a significant additional increase of swelling rates of the samples which were previously sonicated during preparation at the stage of reaction mixture as described in Example 1. These data are presented in the Table 4.

TABLE 4

Effect of additional sonication ot dry samples (dry sonication), which were previously sonicated during preparation at the stage of reaction mixture (wet sonication), on their swelling rates (expressed in the same units as in the Table 1)

| Samples | Swelling rates at time intervals | | | |
|---|---|---|---|---|
|  | 15 sec | 5 min | 1 hour | 24 hours |
| Wet-sonicated | 1.85 | 5.07 | 6.63 | 9.24 |
| Wet-sonicated + Dry sonicated | 2.36 | 8.25 | 10.90 | 13.69 |

The increase of the swelling rates during additional sonication of dry samples may be explained in the same way as in the case of compression of strongly crosslinked dry samples (Example 4); i.e. sonication of dry samples cause additional breakage of partitions between the pores of the sample thus causing a formation of a more branched system of intercommunicating open pores.

EXAMPLE 6

Presence of Strongly and Weakly Bound Water in Samples Prepared Using Sonication This example illustrates the effectiveness of water absorbance by the porous superabsorbent foams of the present invention.

This experiment was performed on the moderately crosslinked samples prepared in the same way as in example 1 except that the concentration of GA was higher at 0.75% and their overall absorption capacity was 11.5 grams of absorbed water per gram of dry sample.

A swelled sample was placed on the nylon microporous filter (pore diameter 0.45 micron) which was put on the sintered glass filter placed on a metal grid to provide mechanical stability during compression of the swelled sample.

The experiment consisted of squeezing out water from the swelled sample by applying mechanical pressure. 6.3 grams of water (54.8%) were expelled from the sample using a relatively low pressure of about 20 Bar. Another 1.2 grams (10.4%) of water were squeezed out under high pressure of 1000 Bar. The residual 4.0 grams (approximately 34%) of water could not be squeezed from the sample even at this pressure and could only be eliminated by subsequently vacuum drying.

It will be appreciated that the residual strongly bound water is likely to be bound by molecular forces within the gel-like network comprising the partitions between pores of the sample while the weakly bound water is retained within the pores volume by capillary forces.

It is noted that, the use of sonication in the formation of superabsorbent polymers is not limited to polymers made by cross-linking of natural polymers such as collagen but is generally applicable to other synthetic polymers as is disclosed in the examples hereinafter.

EXAMPLE 7

This example demonstrates the effect of sonication of a reaction mixture on the absorption properties of synthetic polyacrylate samples prepared without use of blowing agent.

EXPERIMENTAL CONDITIONS

The experimental conditions were essentially the same as described in Example 1 except the following:
1) The temperature of the reaction mixture was maintained in the range of 78–82° C.;
2) The reaction mixture was bubbled with nitrogen (flow rate of about 2–2.5 liter of gaseous nitrogen per minute), the bubbling was started 4–5 min before initiating the reaction by addition of the radical polymerization initiator and was continued until the solidification of the reaction mixture;
3) The duty cycle was 70% and the sonifier output control was set to 7–8;
4) The total volume of the reaction mixture was 20 ml;
5) The vibrating disc of the sonifier tip which contacted to the reaction mixture was covered with a thin layer of a clear silicone sealer available from Dynatron/Bondo Corp., GA, USA, to prevent adhesion of polyacrylate formed during the reaction to the metallic surface of the disc.

Composition of the Reaction Mixture and Preparation of Samples.

The reaction mixture for polyacrylate formation contained 6 grams of acrylic acid 75% neutralized to sodium acrylate (monomer), 25 milligrams of N,N'-methylbisacrylamide (crosslinker), 0.36 grams of Tween-20 (surfactant) and 70 milligrams of potassium persulfate (initiator of radical polymerization reaction) in a total volume of 20 ml. All these chemicals were obtained from Aldrich Chemical Co., WI, USA and used as purchased without additional purification.

The 75% neutralized acrylic acid was prepared by placing 86 grams of acrylic acid in a glass flask and slowly adding to it under constant stirring a solution made by dissolving 36 grams of sodium hydroxide in 175 ml of deionized water. After cooling to room temperature the resulting solution was a 40% w/v solution of 75% neutralized acrylic acid.

Samples were prepared in the following way: 15 ml of hot (85–90° C) 40% (w/v) solution of acrylic acid (neutralized for 75% to sodium acrylate) were placed in the vessel for sonication treatment as disclosed in Example 1. 25 milligrams of dry N,N'-methylbisacrylamide and 3,6 ml of 10% (w/v) solution of Tween-20 were added. The mixture was then stirred by a magnetic stirrer set to a rotation speed of 300 rpm until complete dissolution of N,N'-methylbisacrylamide and bubbled for 4–5 min under continued stirring with gaseous nitrogen (2–2.5 liter per minute). Nitrogen was introduced into the reaction mixture through a tube with an external diameter of 3 mm and an internal diameter of 2 mm. The tube was inserted into the vessel under the disk of the sonifier tip to such a level as to not interfere the rotation of the magnetic rod.

The reaction was started by addition of 1.4 ml of 5% solution of potassium persulfate and the sonication treatment was applied as disclosed in Example 1 until solidifying the reaction mixture due to formation of polyacrylate from the acrylate monomer. The required temperature (80±2° C.) was maintained by means of heating the plate of the magnetic stirrer and also by the heat generated by the vibrating disc of the sonifier tip.

Samples without sonication treatment were prepared in the same way as the sonicated samples except that the sonifier was not switched on during the polymerization reaction. To compensate for the absence of heating of the non-sonicated samples due to applied sonication energy, the required temperature of (80±2° C.) was maintained by more intensive heating of the plate of the magnetic stirrer. It is noted that, the application of sonication treatment markedly decreased the reaction time defined as the time interval between the moment of starting the reaction by addition of initiator and the moment of solidification of the reaction mixture. The reaction time was about 4–5 min in the sonicated samples and about 10–12 min in the non-sonicated samples.

Due to presence of a relatively high concentration of surfactant (Tween-20) in the reaction mixture it solidified in the form of a foam. The foam formed in the sonicated samples and in the non-sonicated samples which were stirred and bubbled without sonication. However, sonication significantly increased foaming efficiency.

After treatment the solidified foamed samples were stored for about 2 hours at 80° C. at ambient atmospheric pressure and then dried overnight in a vacuum oven at 70° C.

Measurement of WAC of Polyacrylate Samples

Figure 13:
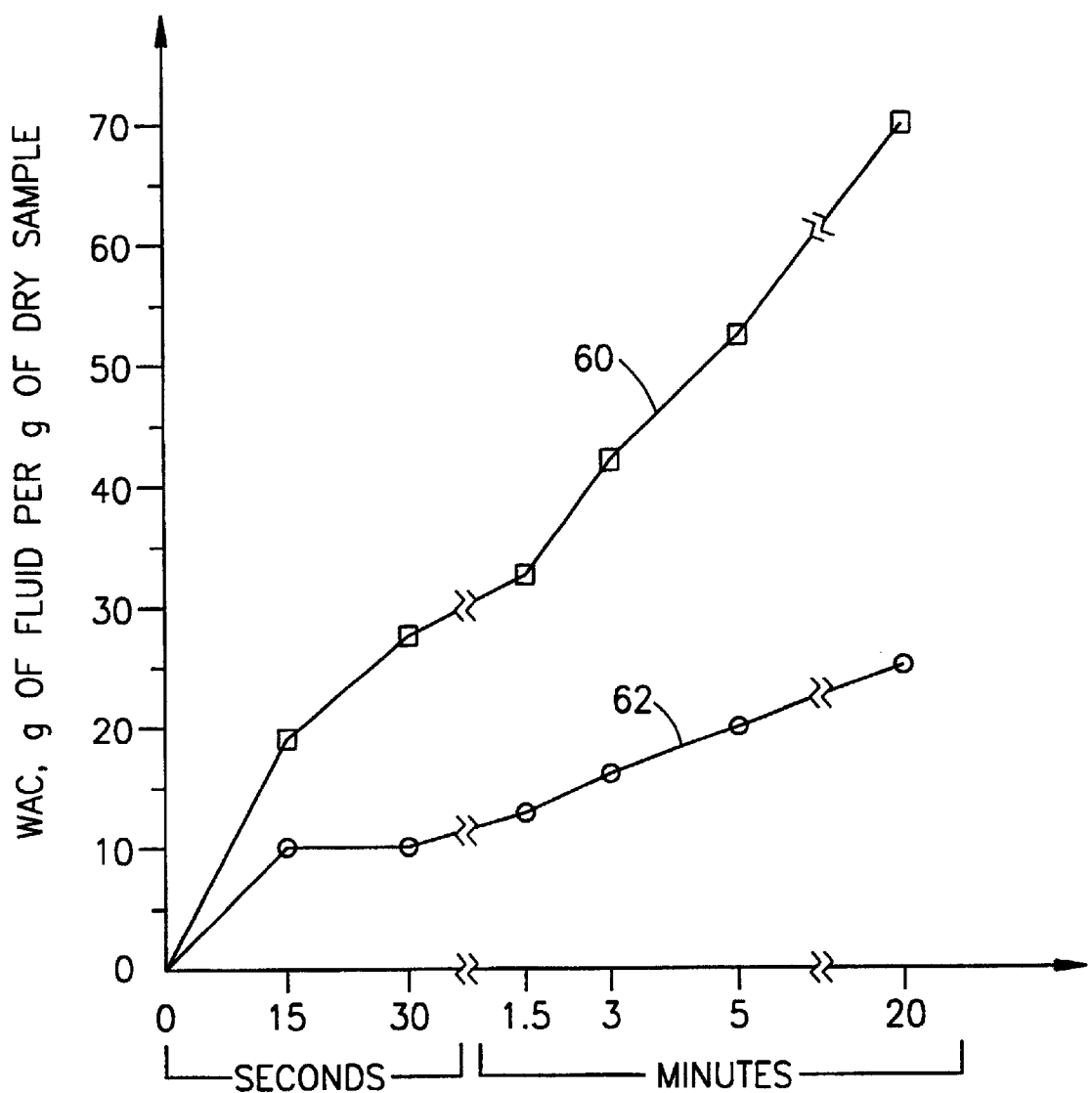
FIG. 13 is a graph illustrating the effect of sonication of reaction mixture on water absorbing capacity of polyacrylate samples prepared without a blowing agent.

Water absorption capacity of dried polyacrylate samples was evaluated as disclosed for the collagen samples of Example 1 hereinabove, except that swelling was performed at room temperature and tap water was used as swelling medium in all experiments unless otherwise stated. FIG. 13, to which reference is now made, is a graph illustrating the swelling capacity of polyacrylate represented on the Y-axis versus time represented on the X-axis, for three time ranges. The curve labeled 60 represents the WAC values of a sonicated polyacrylate sample and the curve labeled 62 represents the WAC values for a non-sonicated polyacrylate sample. The non-sonicated sample was prepared in the same way as the sonicated sample but without using sonication treatment. At all time intervals the WAC values of the sonicated samples exceed the WAC values of the non-sonicated samples by a factor of about 2–3.

EXAMPLE 8

This example demonstrates the effect of sonication of a reaction mixture on the absorption properties of polyacrylate samples prepared with using a blowing agent.

The experiments were performed essentially in the same way as in Example 7 except that, in addition to 20 ml of reaction mixture, the reaction vessel contained 7 ml of 1,1,2-trichlorotrifluoroethane, a volatile organic liquid having a boiling point of 47–48° C., which is immiscible with water, and which was used as a blowing agent. Since the reaction mixture was heated to about 80° C. during the run of the reaction, this organic liquid was intensively evaporated causing efficient foaming.

Figure 14:
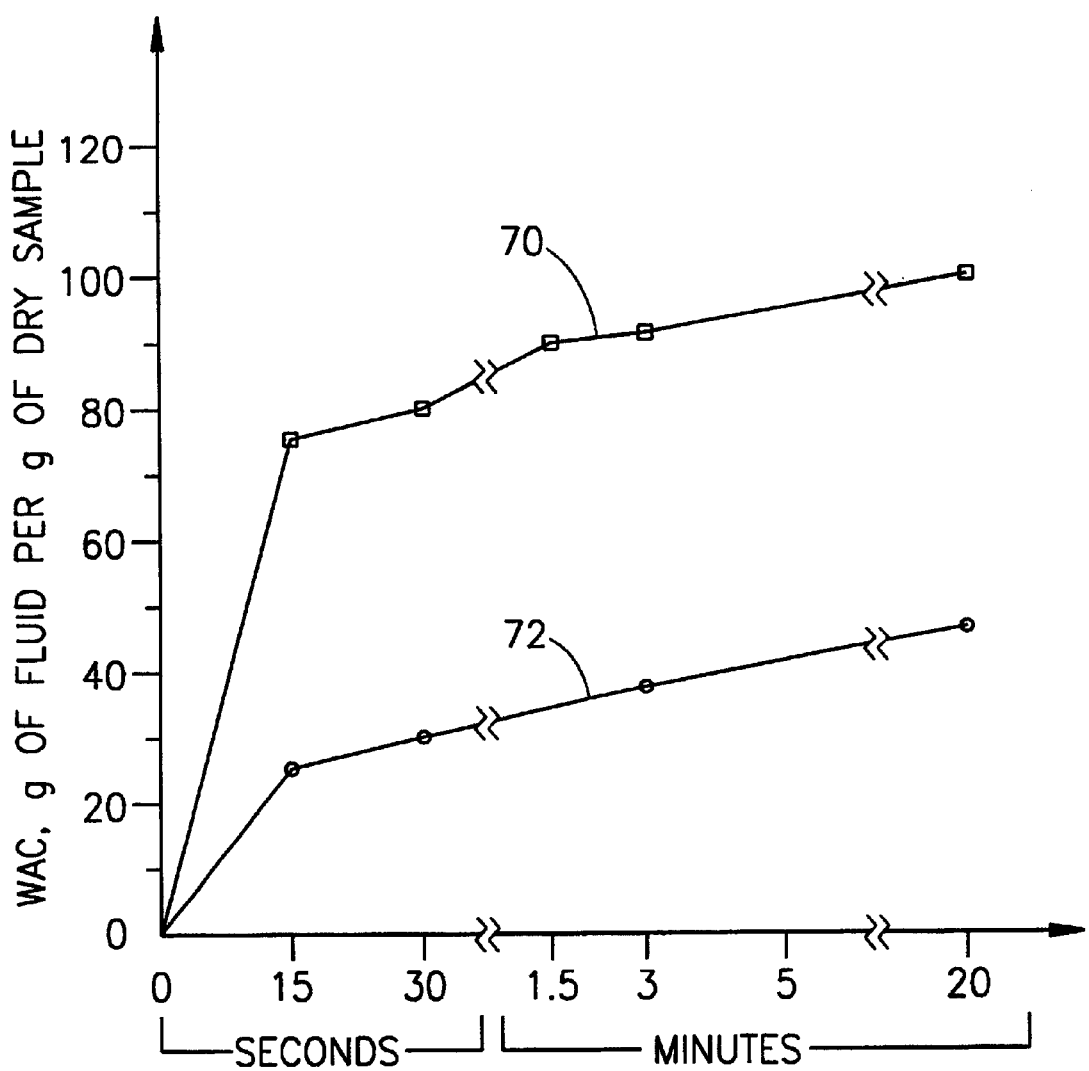
FIG. 14 is a graph illustrating the effect of sonication of reaction mixture on water absorbing capacity of polyacrylate samples prepared with use of a blowing agent.

Reference is now made to FIG. 14 which is a graph representing the WAC values of sonicated and non-sonicated samples of polyacrylate obtained with use of the foaming agent. The curve labeled 70 represents the data for sonicated samples and the curve labeled 72 represents the data for non-sonicated samples. Applying sonication during the run of the reaction markedly increases WAC values at all the time intervals by a factor of about 2.5–3.5 as compared with non-sonicated samples.

EXAMPLE 9

This example demonstrates the effect of sonication of a reaction mixture on the absorption properties of powdered polyacrylate samples prepared by using a blowing agent.

The powdered form of polyacrylate absorbent is important for hygienic applications since it is used as an absorbing constituent in diapers, adult incontinence pads and similar hygienic articles. Polyacrylate samples in powdered form were obtained by grinding of dry solid polyacrylate samples prepared as described in example 8, in a laboratory mill. The size of the particles in the powder was in the range of 0.05–0.3 mm.

The water absorption capacity of the powdered samples was determined by a "tea bag" method. A weighed sample of powder of about 0.15–0.20 grams was placed within a sealable tea bag material having a size of approximately 6×6 cm and sealed. A second tea bag without polymer was prepared. Both tea bags were dipped for 15 seconds in tap water or in a phosphate-buffered saline (PBS) solution, depending on the goal of the experiment (measurement of absorption capacity in water or in PBS). After the 15 second soaking period the bags were removed and hanged upright for 1 minute to drain the excess of water or PBS.

After the draining period, the weight W1 of the tea bag with polyacrylate powder and the weight W2 of the tea bag without powder were recorded. The WAC value for the 15 seconds swelling time was calculated as $(W1-W2)/WO$ wherein WO is the weight of dry powder put initially into the bag. The WAC value is given as the quantity of grams of water absorbed per 1 gram of dry powder. After recording weights of both bags (with and without powder) the bags were again dipped into water or PBS for 15 seconds and the measurement procedure was repeated giving the WAC value for a time of 1.5 min swelling and so on up to a total swelling time of 20 min.

Figure 15:
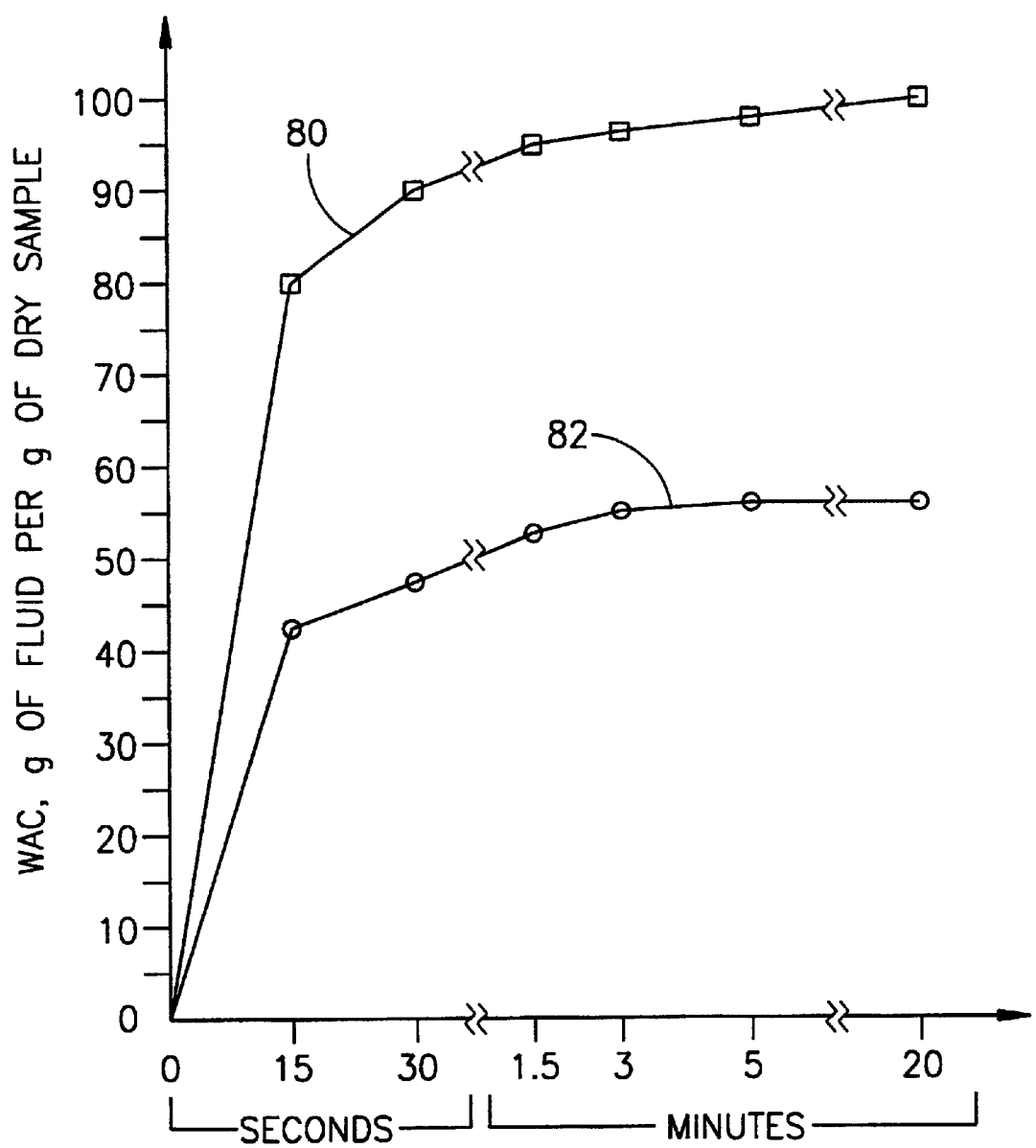
FIG. 15 is a graph illustrating the effect of sonication of reaction mixture on water absorbing capacity of powdered polyacrylate samples in water.
Figure 16:
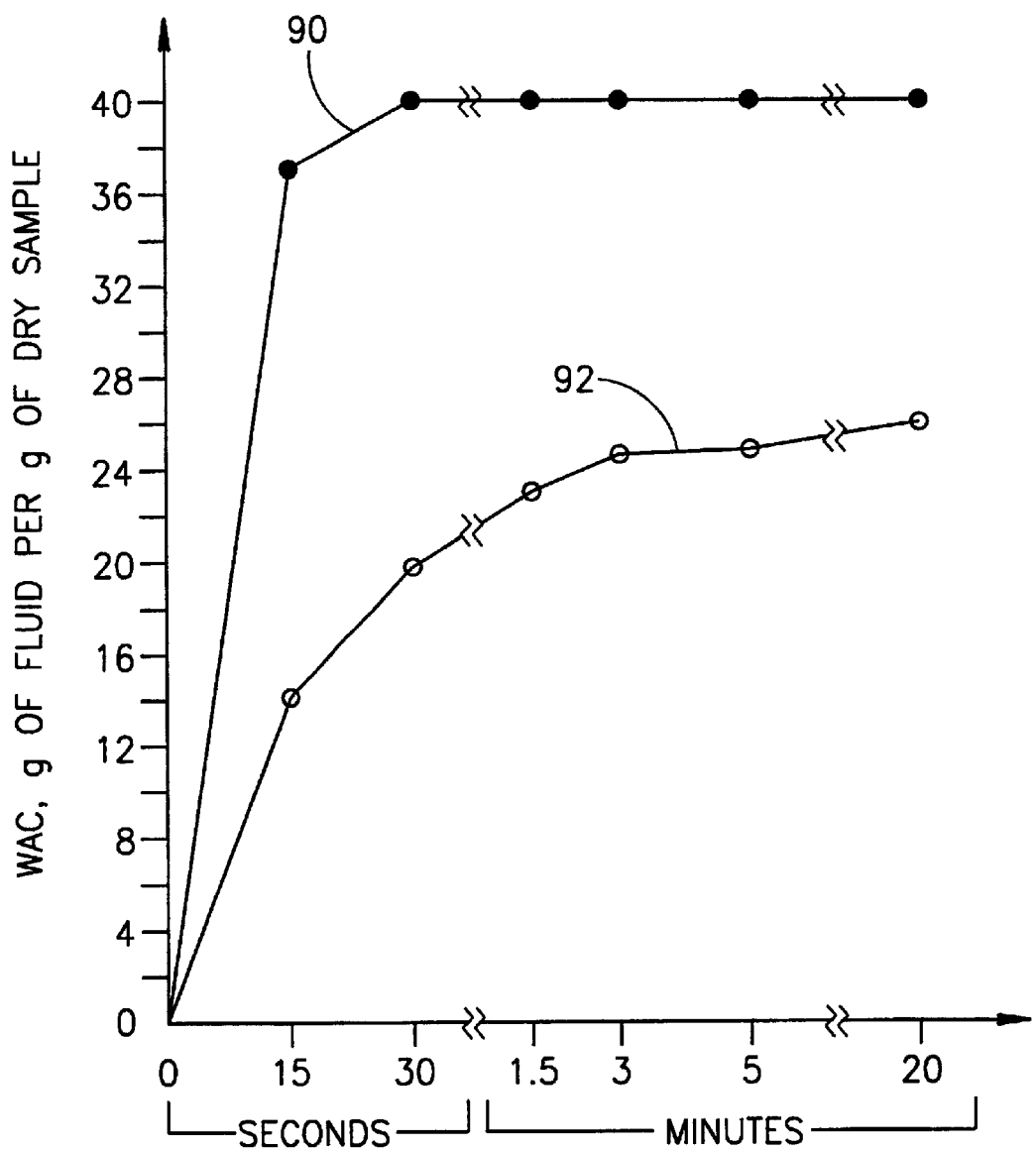
FIG. 16 is a graph illustrating the effect of sonication of reaction mixture on water absorbing capacity of powdered polyacrylate samples in phosphate-buffered saline.

Reference is now made to FIGS. 15 and 16 which are graphs illustrating the WAC values of powdered polyacrylate samples. FIG. 15 illustrates the WAC values in water of sonicated and non-sonicated powdered polyacrylate. the Y-axis represents the WAC in water and the X-axis represents the time. The curve labeled 80 represents the WAC data of a sample of powdered polyacrylate prepared by using sonication treatment and the curve labeled 82 represents the WAC data of a powdered polyacrylate prepared without sonication.

FIG. 16 illustrates the WAC values in PBS of sonicated and non-sonicated powdered polyacrylate in PBS. the Y-axis represents the WAC values in PBS and the X-axis represents the time. The curve labeled 90 represents the WAC data in PBS of a sample of powdered polyacrylate prepared with use of sonication treatment and the curve labeled 92 represents the WAC data in PBS of a powdered polyacrylate prepared without sonication. Both sonicated and non-sonicated samples have lower WAC values in PBS than in water. This is a well-known feature of polyacrylate polymer. However, in water as well as in PBS, the WAC values of sonicated powdered samples markedly exceed those of the non-sonicated powdered samples.

The swelling behavior of polyacrylates in PBS mimics to some extent the swelling behavior in urine. It is noted that, in PBS, the maximal difference in WAC values between sonicated and non-sonicated samples is observed at the shortest time interval of 15 seconds (37 and 15 g/g respectively, FIG. 16). Rapid swelling kinetics is of major importance for absorbent powders used in diapers since urine should be eliminated from baby's skin surface as soon as possible to prevent skin irritation.

EXAMPLE 10

This example demonstrates the efficiency of a scaled up version of the apparatus for producing the superabsorbent foam of the present invention.

Figure 17:
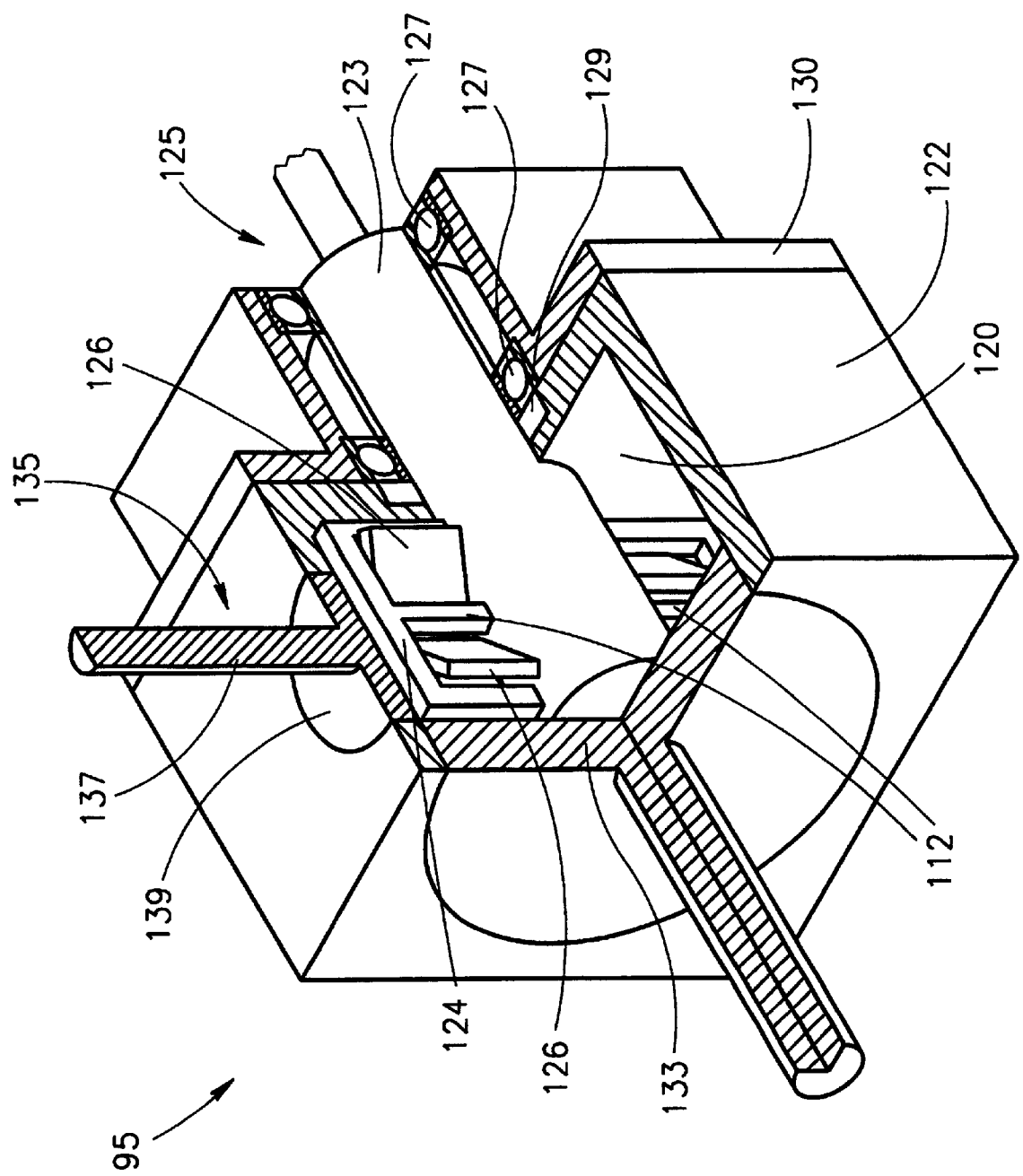
FIG. 17 is a schematic perspective cutaway view of a scaled up reactor in accordance with another preferred embodiment of the present invention.

Reference is now made to FIG. 17 illustrating a scaled up reactor 95 for producing superabsorbent foam. The scaled up reactor 95 includes a housing 122 which has a cylindrical reaction chamber 120 therein. The reaction chamber 120 has a diameter of 12 cm and a length of 5 cm. The housing 122 is made from perspex but can be made from any other suitable material.

The scaled up reactor 95 also includes a stirring unit 125 which includes a shaft 123 having a diameter of 5 cm and two blades 112 attached to the shaft 123. Each of the blades 112 includes a frame 124 and two movable blade sections 126. the blade sections 126 are rotatably attached to the frame 124 as disclosed for the preferred embodiment of stirring unit 103 of FIG. 9. The movable blade sections 126 can be rotated so that the angle between the movable blade sections 126 and the plane of the frame 124 can vary between 0 and 90 degrees.

The scaled up reactor 95 further includes a rear wall 130. The shaft 123 is rotatably attached to the rear wall 130 by means of two ball bearings 127. the shaft 123 is also attached to an electrical motor (not shown) providing a continuously controlled rotation speed of the shaft 123 in the range of 1–1000 rpm. To prevent leakage of the reaction mixture through the gap between the housing 122 and the shaft 123, a ball seal 129 is positioned between the housing 122 and the rear wall 130, around the shaft 123. The ball seal 129 is designed for shafts having a diameter of 5 cm and is a product of Ball Seal Engineering Company, Santa Ana, Calif., USA.

The scaled up reactor 95 also includes a source of sonication energy 135. The source of sonication energy 135 includes a 0.5" probe labelled 137 of a Branson model 450 sonifier (the sonifier is not shown) and a stainless steel disc 139 attached to one end of the probe 137. The disc 139 has a diameter of 3.5 cm and a thickness of 1 mm. The disc is 139 positioned within the wall of the housing 122 such as to directly contact with the internal volume of the reaction chamber 120. The scaled up reactor 95 further includes a removable piston 133. After the completion of the reaction, the piston 133 can be removed and the solidified contents within the reaction chamber 120 can be removed from the chamber.

The working volume of the scaled up reactor 95 is approximately 460 ml which is the volume of the reaction chamber 120 minus the volume of the shaft 123 and the blades 112.

Composition of the Reaction Mixture

The reaction mixture used in this example was the same reaction mixture used for the preparation of loosely crosslinked collagen superabsorbent foam in Example 1 hereinabove.

EXPERIMENTAL CONDITIONS

Sonication treatment was performed at a constant frequency of 20 KHz, in pulse mode with pulse duration of 0.5 sec. The reaction mixture was sonicated using two sonication time intervals $T_1$ and $T_2$. The duration of each of the time intervals $T_1$ and $T_2$ was 4 minutes. The time intervals $T_1$ and $T_2$ were separated by a third time interval of approximately 1 minute for changing the sonication energy output (SEO). A quantity of approximately 200 ml of the reaction mixture were put in the reactor. The reaction was initiated by adding the appropriate amount of the crosslinker glutaraldehyde as disclosed in Example 1 and switching on the stirring and sonication devices. During the reaction the quantity of the reaction mixture increased to approximately 460 ml due to foaming. Ten different experiments were performed using different operating conditions. The WAC values of the superabsorbent foam samples obtained in the ten different experiments are presented in Table 5.

TABLE 5

| Exp. No. | RS (rpm) | SEO (Watts) $T_1$ | SEO (Watts) $T_2$ | Angle of Blade Sections (degrees) | WAC(g/g) for swelling time 15 sec. | WAC(g/g) for swelling time 5 min. | WAC(g/g) for swelling time 60 min. |
|---|---|---|---|---|---|---|---|
| 1 | 300 | 0 | 0 | 0 | 1.6 | 4.0 | 7.6 |
| 2 | 300 | 60 | 60 | 0 | 4.7 | 8.6 | 11.2 |
| 3 | 300 | 60 | 60 | 30 | 5.2 | 10.7 | 12.5 |
| 4 | 300 | 120 | 80 | 30 | 4.8 | 12.1 | 15.2 |
| 5 | 600 | 120 | 80 | 30 | 5.2 | 13.0 | 16.8 |
| 6 | 600 | 120 | 150 | 30 | 6.9 | 13.6 | 21.6 |
| 7 | 600 | 150 | 150 | 45 | 7.6 | 14.7 | 24.5 |
| 8 | 600 | 120 | 180 | 45 | 8.3 | 17.8 | 28.7 |
| 9 | 600 | 180 | 120 | 45 | 8.8 | 18.3 | 28.4 |
| 10 | 600 | 180 | 180 | 45 | 9.5 | 18.3 | 28.4 |

Wherein SEO represents the sonication energy output in watts of the first sonication time interval $T_1$ and the second sonication time interval $T_2$ and RS represents the rotation speed of the stirring device.

The results in Table 5 demonstrate that the WAC values for superabsorbent foam obtained from the scaled up reactor 95 at certain operating parameters are close to and can even exceed the WAC values which were obtained in the smaller laboratory reactor which was used in Examples 1–9. For example, in experiment 8 of Table 5, using a reaction mixture volume of 200 ml, the WAC value at 60 minutes swelling time was 28.7 g/g, compared to a WAC value of 27.9 obtained using a reaction volume of 25 ml in the smaller laboratory reactor of Example 1.

It will be appreciated that the present invention is not limited by what has been described hereinabove and that numerous modifications, all of which fall within the scope of the present invention, exist. For example, while the present invention has been described with respect to collagen and polyacrylate, it is equally applicable to any material capable of forming superabsorbent foam and is not limited to any class of chemical compositions as in the prior art.

Another example is that, while the present invention has been described with respect to application of ultrasonic and audible waves, any suitable waves such as non-linear waves which are shock waves produced by means of electrohydraulic effect or in some other way, may be used in the formation of the superabsorbent foam.

A further example is that, while some of the preferred embodiments of method and apparatus of the present invention include applying ultra-violet light to the reaction mixture in the reactor for cross-linking of the polymer molecules, other forms of physical energy such as visible light and ionizing radiation can be applied to the reaction mixture for inducing cross-linking of the polymer molecules. Additionally, physical energy such as microwave radiation can also be applied to the reaction mixture for raising its temperature, thus, increasing the rate of polymerization and cross-linking reactions. Thus, any of the physical energy forms disclosed hereinabove or any combination thereof can be applied to the reaction mixture for assisting the formation of a superabsorbent foam.

It will be appreciated by persons skilled in the art that the present invention is not limited by what has been particularly shown and described herein above. Rather the scope of the invention is defined by the claims which follow:

What is claimed is:

1. A method for producing a superabsorbent foam, the method comprising the steps of:
    forming a reaction mixture comprising at least one compound capable of forming a superabsorbent foam;
    stirring said reaction mixture; and
    applying mechanical waves selected from ultrasonic waves and sonic waves to said reaction mixture to form said superabsorbent foam.

2. The method according to claim 1 wherein said step of applying comprises continuously applying said mechanical waves to said reaction mixture.

3. The method according to claim 1 further comprising alternating the pressure of said reaction mixture during the forming of said superabsorbent foam.

4. The method according to claim 3 wherein said alternating comprises employing a blowing agent under alternating pressure values.

5. The method according to claim 1 further comprising the steps of drying said superabsorbent foam, and sonicating the dry superabsorbent foam.

6. The method according to claim 1 further comprising the step of compressing said superabsorbent foam.

7. The method according to claim 1 wherein said reaction mixture comprises a natural polymer.

8. The method according to claim 1 wherein said reaction mixture comprises a synthetic polymer.

9. The method according to claim 1 wherein said at least one compound is a monomer capable of being polymerized.

10. The method according to claim 9 wherein said monomer is acrylic acid.

11. The method according to claim 1 wherein said step of applying further comprises the step of applying physical energy to said reaction mixture, wherein said physical energy is selected from the group consisting of ultraviolet light, visible light, ionizing radiation, microwave radiation and any combination thereof.

12. A porous superabsorbent foam substantially comprised of a polymer, wherein said polymer is formed by applying sonic waves or ultrasonic waves to a stirred reaction mixture during a polymerization reaction adapted for forming said polymer.

13. A porous superabsorbent foam substantially comprised of a cross-linked polymer, wherein said cross-linked polymer is formed by applying sonic waves or ultrasonic waves to a stirred reaction mixture including a polymer capable of being cross-linked, said applying is performed during a cross-linking reaction adapted for forming said cross-linked polymer.

14. The method according to claim 1 wherein said step of applying comprises intermittently applying said mechanical waves to said reaction mixture.

15. The superabsorbent foam produced by the method of claim 1.

16. A porous superabsorbent foam substantially comprised of a polymer, said polymer is formed by applying sonic waves or ultrasonic waves to a stirred reaction mixture during a polymerization reaction adapted for forming said polymer, said reaction mixture comprises at least one monomer capable of being polymerized.

17. The porous superabsorbent foam according to claim 16 wherein said reaction mixture further comprises a polymerization initiator.

18. The porous superabsorbent foam according to claim 16 wherein said reaction mixture is stirred during at least part of the duration of said polymerization reaction.

19. The porous superabsorbent foam according to claim 16 wherein said reaction mixture further comprises a surfactant.

20. A porous superabsorbent foam substantially comprised of a cross-linked polymer, said cross-linked polymer is formed by applying sonic waves or ultrasonic waves to a reaction mixture comprising at least one monomer capable of being polymerized and cross-linked, said applying is performed during a polymerization and cross-linking reaction adapted for forming said cross-linked polymer.

21. The porous superabsorbent foam according to claim 20 wherein said reaction mixture further comprises a polymerization initiator.

22. The porous superabsorbent foam according to claim 20 wherein said reaction mixture is stirred during at least part of the duration of said polymerization and cross-linking reaction.

23. The porous superabsorbent foam according to claim 20 wherein said reaction mixture further comprises a crosslinking agent.

24. The porous superabsorbent foam according to claim 20 wherein said reaction mixture further comprises a surfactant.

25. A method for producing a superabsorbent foam, the method comprising the steps of:
    forming a reaction mixture comprising at least one compound capable of forming a superabsorbent foam;
    stirring said reaction mixture; and
    applying non-linear mechanical waves to said reaction mixture to form said superabsorbent foam.

26. The method according to claim 25 wherein said non-linear mechanical waves are shock-waves.

27. A method for producing a superabsorbent foam, the method comprises applying to a stirred reaction mixture mechanical waves selected from the group consisting of ultrasonic waves, sonic waves, non-linear mechanical waves, and shock waves, said reaction mixture comprises at least one compound capable of forming a superabsorbent foam.

28. The method according to claim 27 wherein said reaction mixture is a polymerization reaction mixture, and said at least one compound comprises a monomer capable of undergoing a polymerization reaction to form a polymer.

29. The method according to claim 28 wherein said reaction mixture further comprises a polymerization initiator.

30. The method according to claim 27 further comprising applying physical energy to said reaction mixture to assist the formation of said superabsorbent foam, wherein said physical energy is selected from the group consisting of ultraviolet light, visible light, ionizing radiation, microwave radiation and any combination thereof.

31. The method according to claim 28 wherein said polymerization reaction mixture also comprises a cross-linking agent, and said polymer is a cross-linked polymer.

32. The method according to claim 31 wherein said reaction mixture further comprises a polymerization initiator.

33. The method according to claim 31 further comprising applying physical energy to said reaction mixture to assist the formation of said superabsorbent foam, wherein said physical energy is selected from the group consisting of ultraviolet light, visible light, ionizing radiation, microwave radiation and any combination thereof.

* * * * *

UNITED STATES PATENT AND TRADEMARK OFFICE
CERTIFICATE OF CORRECTION

PATENT NO. : 6,310,113 B1
DATED : October 30, 2001
INVENTOR(S) : Reichman, Eliezer et al.

It is certified that error appears in the above-identified patent and that said Letters Patent is hereby corrected as shown below:

<u>Title page,</u>
Item [75], should read as follows: -- [75] Inventors: Eliezer Reichman; Arkady Skibinsky, both of Rehovot; Diana Kumin, Rishon LeZion, all of (IL) --

Signed and Sealed this

Eighteenth Day of June, 2002

*Attest:*

*Attesting Officer*

JAMES E. ROGAN
*Director of the United States Patent and Trademark Office*